US010221402B2

(12) United States Patent
Rosenberg

(10) Patent No.: US 10,221,402 B2
(45) Date of Patent: Mar. 5, 2019

(54) PRODUCTION OF HIGHLY THERMALLY STABLE RECOMBINANT CHOLINESTERASES FOR THE DETECTION, DETOXIFICATION AND DECONTAMINATION OF ORGANOPHOSPHORUS COMPOUNDS

(71) Applicant: Yvonne Rosenberg, Washington, DC (US)

(72) Inventor: Yvonne Rosenberg, Washington, DC (US)

(73) Assignee: PlantVax, Inc., Rockville, MD (US)

( * ) Notice: Subject to any disclaimer, the term of this patent is extended or adjusted under 35 U.S.C. 154(b) by 0 days.

(21) Appl. No.: 15/126,296

(22) PCT Filed: Mar. 14, 2015

(86) PCT No.: PCT/US2015/020623
§ 371 (c)(1),
(2) Date: Sep. 15, 2016

(87) PCT Pub. No.: WO2015/142679
PCT Pub. Date: Nov. 24, 2015

(65) Prior Publication Data
US 2017/0081649 A1 Mar. 23, 2017

Related U.S. Application Data

(60) Provisional application No. 61/953,893, filed on Mar. 16, 2014.

(51) Int. Cl.
*C12N 9/18* (2006.01)
*C07K 7/08* (2006.01)
*A61K 38/46* (2006.01)
*A61K 47/36* (2006.01)
*A62D 3/02* (2007.01)
*C12Q 1/46* (2006.01)
*A61K 38/00* (2006.01)
*A62D 101/02* (2007.01)
*A62D 101/26* (2007.01)

(52) U.S. Cl.
CPC .............. *C12N 9/18* (2013.01); *A61K 38/465* (2013.01); *A61K 47/36* (2013.01); *A62D 3/02* (2013.01); *C07K 7/08* (2013.01); *C12Q 1/46* (2013.01); *C12Y 301/01008* (2013.01); *A61K 38/00* (2013.01); *A62D 2101/02* (2013.01); *A62D 2101/26* (2013.01); *C07K 2319/04* (2013.01); *C07K 2319/21* (2013.01); *C07K 2319/43* (2013.01)

(58) Field of Classification Search
CPC .............. C12Q 1/46; C12Y 301/01007; C12Y 301/01008
See application file for complete search history.

(56) References Cited

U.S. PATENT DOCUMENTS 8,168,175 B2 * 5/2012 Rosenberg ........... A61K 9/0075
424/406
2014/0090108 A1 * 3/2014 Garabagi ........... C12N 15/8257
800/288
2017/0081649 A1 3/2017 Rosenberg

FOREIGN PATENT DOCUMENTS

| WO | 2008088385 A2 | 7/2008 | |
|---|---|---|---|
| WO | WO 2008/088385 * | 7/2008 | ............... C07K 7/08 |
| WO | 2012094627 A2 | 7/2012 | |
| WO | 2013040572 A2 | 3/2013 | |

OTHER PUBLICATIONS

Chitlaru, T. et al., Biochem. J., 2002; vol. 363, pp. 619-631.*
Kronman, C. et al. Biochem. J., 1995; vol. 311, pp. 959-967.*
Kronman, C. et al. Gene, 1992; vol. 121, pp. 295-304.*
Soreq, H. et al. PNAS Dec. 1990; vol. 87, pp. 9688-9692.*
Duysen, E., Bartels, C. and Lockridge, O., The Journal of Pharmacology and Experimental Therapeutics 2002; vol. 302, No. 2, pp. 751-758.*
Rosenberg, Y. et al. Chemio Biological Interactions 2010; vol. 187, pp. 279-286.*
Geyer, B. et al. BMC Biotechnology, May 30, 2007; pp. 1-14.*
Beckett, A.H. et al. Biochemical Pharmacology 1969, vol. 18, issue 7; pp. 1701-1705.*
International Preliminary Report of Patentability dated Sep. 29, 2016 and received in PCT/US2015/020623.
Rosenberg; et al, A Highly Stable Minimally Processed Plant-Derived Recombinant Acetylcholinesterase for Nerve Agent Detection in Adverse Conditions; Scientific Reports, Aug. 13, 2015.
Rotundo, "Biogenesis, Assembly and Trafficking of Acetylcholinesterase," Journal of Neurochemistry, 142 (Suppl. 2), 2017, pp. 52-58.
International Search Report and Written Opinion from corresponding PCT/US2015/020623, dated Jun. 1, 2015.
Pan et al.,"Model of Human Butyrylcholinesterase (BChE) Tetramer by Homology Modeling and Dynamics Simulation", The Journal of Physical Chemistry B, vol. 113, No. 18, May 7, 2009, pp. 6543-6552, XP55190129.
Rotundo et al., "Assembly and Regulation of Acetylcholinesterase at the Vertebrate Neuromuscular Junction", Chemico-Biological Interactions, vol. 175, No. 1-3, Sep. 25, 2008, pp. 26-29, XP024530498.

(Continued)

Primary Examiner — Russell Kallis
(74) Attorney, Agent, or Firm — Michele Wales; InHouse Patent Counsel, LLC

(57) ABSTRACT

Disclosed herein are methods for the large-scale production of a highly thermally stable acetylcholinesterase (AChE) and butyrylcholinesterase (BChE). Additionally, the expression methods disclosed herein can produce ChE preparations consisting of extract or purified forms that can be produced in high amounts and are highly thermally stable. These ChE products can be used in vitro detection, detoxification and decontamination methods.

46 Claims, 11 Drawing Sheets
Specification includes a Sequence Listing.

(56) References Cited

OTHER PUBLICATIONS

Garabagi et al., "Utility of the P19 Suppressor of Gene-Silencing Protein for Production of Therapeutic Antibodies in Nicotiana Expression Hosts", Plant Biotechnology Journal, vol. 10, No. 9, Dec. 17, 2012, pp. 1118-1128, XP055190195.

* cited by examiner

Figure 1.

Optimized human AChE E4-E6 isoform (SEQ ID NO: 1)

```
ATGAGGCCTCCTCAGTGCCTTCTTCACACTCCATCTCTTGCTAGTCCTTTGTTGCTCTTGCTTC
TTTGGCTTCTCGGAGGTGGTGTTGGAGCTGAAGGTAGAGAAGATGCTGAGCTTCTTGTTACTGT
TAGAGGCGGCCGCTTGAGGGGAATTAGACTTAAGACTCCAGGTGGCCCAGTGTCTGCTTTCCTT
GGTATTCCATTTGCTGAACCACCCATGGGCCCAAGAAGATTTCTTCCACCAGAACCTAAGCAGC
CTTGGTCTGGTGTTGTGAACGCTACTACTTTCCAGTCCGTGTGCTACCAGTATGTGGATACTCT
CTACCCAGGATTCGAGGGCACTGAGATGTGGAATCCAAACCGTGAGCTTTCCGAGGATTGCCTC
TACCTTAACGTGTGGACTCCATACCCAAGGCCAACTTCTCCAACTCCAGTTCTCGTTTGGATCT
ACGGTGGTGGATTCTACTCCGGTGCTTCTTCTCGATGTGTACGATGGAAGATTCCTCGTTCA
GGCTGAGAGGACTGTGCTCGTGTCTATGAATTACAGGGTGGGAGCTTTCGGATTCCTTGCTTTG
CCAGGATCTAGAGAGGCTCCAGGTAACGTTGGACTTCTTGATCAAAGGCTTGCTCTCCAGTGGG
TGCAAGAGAATGTTGCTGCTTTTGGAGGCGATCCAACTTCCGTGACTCTTTTCGGAGAATCTGC
TGGTGCTGCTTCTGTGGGAATGCACCTTTTGTCTCCACCATCTAGGGGACTTTTCCACAGGGCT
GTTCTTCAATCTGGTGCTCCAAATGGACCTTGGGCTACTGTTGGAATGGGAGAGGCTAGAAGAA
GGGCTACTCAGCTTGCTCATCTTGTTGGATGTCCACCAGGTGGAACTGGTGGAAACGATACTGA
GCTTGTTGCTTGCCTTAGGACTAGGCCAGCTCAGGTTTTGGTTAATCACGAGTGGCACGTGCTC
CCACAAGAGTCTGTTTTCAGGTTCTCTTTCGTGCCTGTGGTGGATGGCGATTTCCTCTCTGATA
CTCCTGAAGCTCTCATCAACGCTGGTGATTTCCACGGACTTCAGGTGTTGGTTGGAGTGGTTAA
GGATGAGGGCTCTTACTTCCTTGTGTACGGTGCTCCAGGCTTCTCCAAGGATAACGAGTCTCTC
ATTTCCAGGGCTGAGTTCCTTGCTGGTGTTAGGGTTGGAGTTCCACAGGTGTCAGATCTTGCTG
CTGAGGCTGTTGTGCTCCACTACACTGATTGGCTTCACCCAGAAGATCCAGCTAGGCTTAGGGA
AGCTCTTTCTGATGTTGTGGGCGATCATAACGTTGTGTGCCCAGTTGCTCAACTTGCTGGTAGA
CTTGCTGCTCAGGGTGCTAGGGTTTACGCTTACGTTTTCGAGCACAGGGCTTCCACTTTGTCTT
GGCCACTTTGGATGGGTGTTCCACACGGATACGAGATCGAGTTCATCTTCGGAATCCCACTCGA
TCCATCCCGTAACTACACTGCTGAGGAAAAGATCTTCGCTCAGAGGCTCATGAGGTACTGGGCT
AATTTTGCTAGGACTGGCGATCCTAACGAGCCAAGAGATCCAAAGGCTCCACAATGGCCACCAT
ATACAGCTGGTGCTCAGCAGTACGTGTCCCTTGATCTTAGACCACTTGAGGTGAGAAGGGGACT
TAGGGCTCAAGCTTGCGCTTTCTGGAACAGATTCCTTCCAAAGCTCCTCAACGCTACTGATACT
CTCGATGAAGCTGAGAGGCAATGGAAGGCTGAGTTTCACCGTTGGTCCTCTTACATGGTGCACT
GGAAGAACCAGTTCGATCACTACTCCAAGCAGGATAGGTGCTCTGATTTGTGA
```

Figure 1 cont.

Optimized Macaca AChE (SEQ ID NO: 2)

ATGAGGCCTCCTCAGTGCCTTCTTCATACTCCTAGTCTTGCTTCTCCTCTTCTGCTGCTGCTTC
TTTGGCTTCTTGGTGGTGGTGTTGGTGCTGAAGGTAGAGAAGATGCTGAGCTTCTTGTGACTGT
TAGGGGTGGTAGGCTTAGGGGTATCAGGCTTAAGACTCCTGGTGGTCCTGTGTCTGCTTTCCTT
GGTATTCCTTTTGCTGAGCCTCCTACCGGTCCTAGAAGATTTTTGCCTCCTGAACCTAAGCAGC
CTTGGTCTGGTGTTGTGGATGCTACTACTTTCCAGAGCGTGTGCTACCAGTATGTGGATACCCT
TTACCCTGGTTTCGAGGGAACTGAGATGTGGAACCCTAACAGAGAGCTGTCTGAGGATTGCCTG
TACCTTAATGTGTGGACCCCTTACCCTAGGCCTACTTCTCCTACTCCTGTTCTGGTTTGGATCT
ACGGTGGTGGTTTCTACAGCGGTGCTTCTTCTCTGGATGTGTACGATGGTAGATTCCTGGTTCA
GGCTGAGAGGACTGTGCTGGTGTCTATGAATTACAGGGTGGGAGCTTTCGGTTTCCTTGCTTTG
CCTGGTTCTAGAGAGGCTCCTGGTAACGTTGGTCTTTTGGATCAGAGGCTTGCTCTGCAGTGGG
TGCAAGAAATGTTGCTGCTTTCGGTGGTGATCCTACCTCTGTGACTCTTTTCGGTGAATCTGC
TGGTGCTGCTTCAGTGGGTATGCACCTTTTGTCTCCACCTTCTAGGGGACTTTTCCACAGGGCT
GTTCTTCAATCTGGTGCTCCTAATGGTCCTTGGGCTACTGTTGGTATGGGTGAGGCTAGAAGAA
GGGCTACTCAGCTTGCTCATCTTGTTGGTTGTCCTCCAGGTGGTACTGGTGGTAATGATACTGA
GCTTGTGGCTTGCCTTAGGACCAGACCTGCTCAGGTTTTGGTGAACAATGAGTGGCACGTGCTG
CCTCAAGAGTCTGTGTTTAGGTTCTCTTTCGTGCCTGTGGTGGATGGTGATTTCCTGTCTGATA
CTCCTGAGGCTCTGATCAACGCTGGTGATTTTCACGGACTTCAGGTTCTGGTTGGTGTGGTGAA
GGATGAGGGATCTTACTTCCTTGTGTACGGTGCTCCTGGTTTCAGCAAGGATAACGAGTCTCTG
ATCAGCAGGGCTGAGTTCCTTGCTGGTGTTAGAGTTGGTGTTCCTCAGGTGTCAGATCTTGCTG
CTGAGGCTGTTGTGCTTCACTACACTGATTGGCTGCACCCTGAAGATCCTGCTAGACTTAGGGA
AGCTCTGTCTGATGTGGTGGGTGATCATAATGTTGTGTGCCCTGTTGCTCAGTTGGCTGGTAGA
CTTGCTGCTCAAGGTGCTAGGGTTTACGCTTACGTTTTCGAGCATAGGGCTTCTACCCTTTCTT
GGCCTCTTTGGATGGGAGTGCCTCACGGTTATGAGATCGAGTTCATCTTCGGTATCCCTCTTGA
TCCTTCTAGGAACTACACCACCGAGGAAAAGATCTTCGCTCAGAGGCTGATGAGGTACTGGGCT
AATTTTGCTAGGACTGGTGATCCAAACGAGCCTAGAGATCCTAAGGCTCCTCAATGGCCTCCTT
ATACAGCTGGTGCTCAGCAGTACGTGAGCCTTGATCTTAGACCTCTTGAGGTGAGAAGGGGTCT
TAGGGCTCAAGCTTGCGCTTTCTGGAACAGATTCCTGCCTAAGCTTCTGAGCGCTACCGATACT
CTTGATGAAGCTGAGAGACAGTGGAAGGCAGAGTTCCATAGGTGGTCCTCTTACATGGTGCACT
GGAAGAACCAGTTCGATCACTACAGCAAGCAGGATAGGTGCAGCGATCTTTAG

Figure 1 cont.

```
HuBChE wild type (SEQ ID NO: 3)
GI:148277049
ATGCATAGCAAAGTCACAATCATATGCATCAGATTTCTCTTTTGGTTTCTTTTGCTCTGCATGC
TTATTGGGAAGTCACATACTGAAGATGACATCATAATTGCAACAAAGAATGGAAAAGTCAGAGG
GATGAACTTGACAGTTTTTGGTGGCACGGTAACAGCCTTTCTTGGAATTCCCTATGCACAGCCA
CCTCTTGGTAGACTTCGATTCAAAAAGCCACAGTCTCTGACCAAGTGGTCTGATATTTGGAATG
CCACAAAATATGCAAATTCTTGCTGTCAGAACATAGATCAAAGTTTTCCAGGCTTCCATGGATC
AGAGATGTGGAACCCAAACACTGACCTCAGTGAAGACTGTTTATATCTAAATGTATGGATTCCA
GCACCTAAACCAAAAAATGCCACTGTATTGATATGGATTTATGGTGGTGGTTTTCAAACTGGAA
CATCATCTTTACATGTTTATGATGGCAAGTTTCTGGCTCGGGTTGAAAGAGTTATTGTAGTGTC
AATGAACTATAGGGTGGGTGCCCTAGGATTCTTAGCTTTGCCAGGAAATCCTGAGGCTCCAGGG
AACATGGGTTTATTTGATCAACAGTTGGCTCTTCAGTGGGTTCAAAAAAATATAGCAGCCTTTG
GTGGAAATCCTAAAAGTGTAACTCTCTTTGGAGAAAGTGCAGGAGCAGCTTCAGTTAGCCTGCA
TTTGCTTTCTCCTGGAAGCCATTCATTGTTCACCAGAGCCATTCTGCAAAGTGGATCCTTTAAT
GCTCCTTGGGCGGTAACATCTCTTTATGAAGCTAGGAACAGAACGTTGAACTTAGCTAAATTGA
CTGGTTGCTCTAGAGAGAATGAGACTGAAATAATCAAGTGTCTTAGAAATAAAGATCCCCAAGA
AATTCTTCTGAATGAAGCATTTGTTGTCCCCTATGGGACTCCTTTGTCAGTAAACTTTGGTCCG
ACCGTGGATGGTGATTTTCTCACTGACATGCCAGACATATTACTTGAACTTGGACAATTTAAAA
AAACCCAGATTTTGGTGGGTGTTAATAAAGATGAAGGGACAGCTTTTTTAGTCTATGGTGCTCC
TGGCTTCAGCAAAGATAACAATAGTATCATAACTAGAAAAGAATTTCAGGAAGGTTTAAAAATA
TTTTTTCCAGGAGTGAGTGAGTTTGGAAAGGAATCCATCCTTTTCATTACACAGACTGGGTAG
ATGATCAGAGACCTGAAAACTACCGTGAGGCCTTGGGTGATGTTGTTGGGGATTATAATTTCAT
ATGCCCTGCCTTGGAGTTCACCAAGAAGTTCTCAGAATGGGGAAATAATGCCTTTTTCTACTAT
TTTGAACACCGATCCTCCAAACTTCCGTGGCCAGAATGGATGGGAGTGATGCATGGCTATGAAA
TTGAATTTGTCTTTGGTTTACCTCTGGAAAGAAGAGATAATTACACAAAAGCCGAGGAAATTTT
GAGTAGATCCATAGTGAAACGGTGGGCAAATTTTGCAAAATATGGGAATCCAAATGAGACTCAG
AACAATAGCACAAGCTGGCCTGTCTTCAAAAGCACTGAACAAAAATATCTAACCTTGAATACAG
AGTCAACAAGAATAATGACGAAACTACGTGCTCAACAATGTCGATTCTGGACATCATTTTTTCC
AAAAGTCTTGGAAATGACAGGAAATATTGATGAAGCAGAATGGGAGTGGAAAGCAGGATTCCAT
CGCTGGAACAATTACATGATGGACTGGAAAAATCAATTTAACGATTACACTAGCAAGAAGAAA
GTTGTGTGGGTCTCTAA
```

Figure 1 cont.

MaBChE wild type (SEQ ID NO: 4)

GI:290795732

ATGGATAGCAAAGTCACAATCATATGCATCAGATTACTCTTTTGGTTTCTTTTGCTCTGCATGC
TTATTGGAAAGTCACATACTGAAGATGACATCGTAATTGCAACAAAGAATGGAAAAGTCAGAGG
GATGAACTTAACAGTTCTTGGTGGCACGGTAACAGCCTTTCTTGGAATTCCCTATGCACAGCCA
CCTCTTGGTAGACTTCGATTCAAAAAGCCACAGTCTCTGACCAAGTGGTCTGATATTTGGAATG
CCACAAAATATGCAAATTCTTGCTATCAGAACATAGATCAAAGTTTTCCAGGCTTCCATGGATC
AGAGATGTGGAACCCAAACACTGACCTCAGTGAAGACTGTTTATATCTAAATGTATGGATTCCG
GCACCTAAACCAAAAAATGCTACTGTAATGATATGGATTTATGGTGGTGGTTTTCAGACTGGAA
CATCATCTTTACATGTTTATGATGGCAAGTTTCTGGCTCGAGTTGAAAGAGTTATTGTAGTGTC
AATGAACTATAGGGTGGGTGCCCTTGGATTCTTAGCTTTGCCAGGAAATCCTGAGGCTCCAGGG
AACATGGGTTTATTTGATCAACAGTTGGCTCTTCAGTGGGTTCAAAAAAATATAGCAGCCTTTG
GTGGAAATCCTAAAAGTGTAACTCTCTTTGGAGAAAGTGCAGGAGCAGCTTCAGTTAGCCTGCA
TTTGCTTTCTCCTGGAAGCCATTCATTGTTCACCAGAGCCATTCTACAAAGTGGATCCTCTAAC
GCTCCTTGGGCAGTAACATCTCTTTATGAAGCTAGGAACAGAACATTGACCTTGGCTAAATTGA
CTGGTTGCTCTAGAGATAATGAGACTGAAATAGTCAAGTGCCTTAGAAATAAAGATCCCCACGA
AATTCTTCTGAATGAAGCATTTGTTGTCCCCTATGGGACTCTCTTGTCAGTAAACTTCGGTCCA
ACCATGGATGGTGATTTTCTCACTGAAATGCCAGACATATTACTTGAACTTGGACAATTTAAAA
AAACCCAGATATTGGTGGGTGTTAATAAAGATGAAGGGACAGCTTTTTAGTCTATGGTGCTCC
TGGCTTCAGCAAAGATAACGATAGTATCATAACTAGAAACGAATTTCAGGAAGGTTTAAAAATA
TTTTTTCCAGGCGTGAGTGAGTTTGGAAAGGAATCCATCCTTTTCATTACACAGACTGGGTAG
ATGATCAGAGACCTGAAAACTACCGTGAGGCGTTGGATGATGTTGTTGGGGATTATAATATCAT
ATGCCCTGCCTTGGAGTTTACCAAGAAGTTCTCAGAATGGGGAAATAATGCCTTTTTCTACTAT
TTTGAACACCGATCCTCCAAACTTCCGTGGCCAGAATGGATGGGAGTGATGCATGGCTATGAAA
TTGAATTTGTCTTTGGTTTACCTCTGGAAAGAAGAGTTAATTACACAAAAGCTGAGGAAATTTT
GAGTAGATCCATAGTGAAACGGTGGGCAAATTTTGCAAAATATGGGAATCCAAATGGGACTCAT
AATAATAGCACAAAATGGCCTGTCTTCAAAAGCACTGAACAAAAATATCTAACCTTGAATACAG
AGTCATCAAGAATATTGACTAAACTACGTGCTCAGCAATGCCGATTCTGGACATCATTTTTTCC
AAAAGTCTTGGAAATGACAGGAAATATTGATGAAGCAGAATGGGAGTGGAAAGCAGGATTCCAT
CGCTGGAGCAATTACATGATGGACTGGAAAAATCAATTTAACGATTACACTAGCAAGAAAGAAA
GTTGTGTGGGTCTCTAA

Figure 1 cont.

```
PRAD (SEQ ID NO: 5)

ATGGCTGTCCTGAATCCAATGACTTTGGGAATTTATCTCCAACTCTTCTTCTGCTCCATCGTGT
CGCAGCCAACTTTCATCAACAGTGTCCTCCCAATCTCAGCAGCCCTTCCTGGCCTGGATCAGAA
GAAACGAGGCAACCACAAAGCATGCTGCCTACTGATGCCCCGCCACCCCCACTCTTCCCACCG
CCATTCTTCGACTACAAGGACGACGATGACAAGTGATAA

Tomato bushy stunt virus partial P19 (SEQ ID NO: 6)
     GI:9663838

ATGGAACGAGCTATACAAGGAAACGACGCTAGGGAACAAGCTAACAGTGAACGTTGGGATGGAG
GATCAGGAGGTACCACTTCTCCCTTCAAACTTCCTGACGAAAGTCCGAGTTGGACTGAGTGGCG
GCTACATAACGATGAGACGAATTCGAATCAAGATAATCCCCTTGGTTTCAAGGAAAGCTGGGGT
TTCGGGAAAGTTGTATTTAAGAGATATCTCAGATACGACAGGACGGAAGCTTCACTGCACAGAG
TCCTTGGATCTTGGACGGGAGATTCGGTTAACTATGCAGCATCTCGATTTTTCGGTTTCGACCA
GATCGGATGTACCTATAGTATTCGGTTTCGAGGAGTTAGTATCACCGTTTCTGGAGGGTCGCGA
ACTCTTCAGCATCTCTGTGAGATGGCAATTCGGTCTAAGCAAGAACTGCTACAGCTTGCCCCAA
TCGAAGTGGAAAGTAATGTATCAAGAGGATGCCCTGAAGGTACTGAGACCTTCGAAAAGAAAG
CGAGTAA
```

PRODUCTION OF HIGHLY THERMALLY STABLE RECOMBINANT CHOLINESTERASES FOR THE DETECTION, DETOXIFICATION AND DECONTAMINATION OF ORGANOPHOSPHORUS COMPOUNDS

The invention was made with Government support under NIH grant No. 1R43NS059247 and DTRA contract No HDTRA1-12-C-0086. The Government may have certain rights to the invention.

FIELD OF THE INVENTION

This invention relates to compositions and methods for the production and use of cholinesterases with improved thermal stability. In particular, it relates to methods for the production of highly stable cholinesterases for use in the detection, detoxification and decontamination of organophosphorus compounds.

DESCRIPTION OF THE RELATED ART

Exposure and injury from organophosphorus (OP) nerve agents may result from industrial accident (Hardison et al., 2013), military stockpiling, war, or terrorist attack. OP nerve agents disrupt the nervous system by inhibiting the function of the enzyme acetylcholinesterase (AChE; EC 3.1.1.7) via formation of a covalent bond with the active-site serine. Thus, levels of acetylcholine continue to build up in the synapses so that nerve impulses are continually transmitted and muscles keep contracting. Classical nerve agents include G-agents such as soman, sarin, cyclosarin, and tabun and V-agents such as VX and VR. Initial symptoms following exposure to nerve agents (like sarin) are a runny nose, tightness in the chest, and constriction of the pupils. Soon after, the victim experiences difficulty breathing followed by nausea and drooling. As the victim continues to lose control of his/her bodily functions, he/she will involuntarily salivate, lacrimate, urinate, defecate, and experience gastrointestinal pain and vomiting. This phase is followed by myoclonic jerks, status epilepticus, and ultimately death resulting from complete respiratory depression, most likely via the excessive peripheral activity at the neuromuscular junction of the diaphragm (Sidell et al., 1997) Inhibition of AChE may not account for all of the toxic effects of nerve agents. These agents also are known to bind directly to nicotinic receptors and cardiac muscarinic receptors. They also antagonize gamma-aminobutyric acid (GABA) neurotransmission and stimulate glutamate N-methyl-d-aspartate (NMDA) receptors. These latter actions may partly mediate nerve agent-induced seizures and CNS neuropathology.

A number of insecticides, the phenothiazines, organophosphates such as dichlorvos, malathion and parathion, are nerve agents. Malathion is widely used in agriculture, residential landscaping, public recreation areas, and in public health pest control programs such as mosquito eradication. In the US, it is the most commonly used OP insecticide (Bonner et al., 2007). Forty organophosphate pesticides are registered in the U.S., with at least 73 million pounds used in agricultural and residential settings (Bonner et al., 2007). The EPA banned most residential uses of organophosphates in 2001, but they are still sprayed agriculturally on fruits and vegetables and there use is widespread in developing countries. Due to sufficient differences in the metabolism of these compounds by insects and mammals, low doses that are toxic to insects have little effect on humans and other mammals. But, there is considerable concern about the effects of long-term exposure to these chemicals by farm workers and animals alike. At high enough doses, however, acute toxicity and death can occur through the same mechanism as other nerve agents. OP pesticide poisoning is a major cause of disability in many developing countries and is often the preferred method of suicide (Buckley et al., 2004).

Due to their high reactivity with OP compounds, the use of cholinesterases (ChEs), including AChE and butyrylcholinesterase (BChE; EC 3.1.1.8) has been investigated for counteracting the toxicity of these compounds in vivo and for the detection, detoxification and decontamination of these compounds in vitro and in exposed environments. Several studies demonstrated that exogenously administered native AChE from fetal bovine serum or BChE from equine or human (Hu) serum not only protected animals from toxicity of OP nerve agents, but also prevented death in these animals (Ashani et al., 1991; Raveh et al., 1993, 1997). Of the enzymes tested, Hu BChE appears to be most appropriate for human use (Ashani, 2000). It was shown that pretreatment with Hu BChE alone protected mice from toxicity due to soman, sarin, tabun and VX (Ashani et al., 1991; Raveh et al., 1993). In addition to enhancing survivability, pretreatment with Hu BChE prevented the development of soman-induced cognitive impairments in rats (Brandeis et al., 1993) and soman-induced behavioral deficits in rhesus monkeys (Raveh et al., 1997). More recently, the efficacy of Hu BChE was demonstrated in guinea pigs against cumulative s.c. challenges of up to $5.5 \times LD_{50}$ of soman or $8 \times LD_{50}$ of VX (Lenz et al., 2005; Saxena et al., 2011). In these studies, no signs of OP poisoning were observed and all animals survived the duration of challenge. In non-human primates, four of six cynomolgus monkeys were protected against a cumulative challenge of $5.5 \times LD_{50}$ of soman and the four surviving animals did not display any immediate or delayed signs of OP toxicity (Sun et al., 2008).

Since, inhalation is the most likely route of exposure to G-type nerve agents on the battlefield or in public places, the efficacy of Hu BChE was also evaluated against a vapor challenge. Allon et al., reported that exogenously administered Hu BChE protected guinea pigs from inhalation toxicity from nose-only exposure to soman (Allon et al., 1998). More recently, the efficacy of Hu BChE was demonstrated against a whole-body exposure of Göttingen minipigs to a lethal dose of sarin vapor (Saxena et al., 2011a). In addition, HuBChE delivered as an aerosolized pretreatment has been shown to protect macaques against 1-3 LD50 of aerosolized paraoxon given 1-40 hours later (Rosenberg et al., 2013). Since ChEs function as stoichiometric bioscavengers, large quantities of enzymes are needed for therapeutic or detoxification/decontamination purposes. This requirement prompted attempts to develop systems for the expression of large quantities of recombinant ChEs using mammalian cell lines, transgenic goats and transgenic plants (Fischer et al., 1993; Kronman et al., 1992; Chilukuri et al., 2005; Rosenberg et al, 2010; Huang et al., 2007; Evron et al., 2007). While the production of recombinant ChEs is higher in transgenic animals and plants, the goat system is not cost-effective and contains potentially immunogenic non-human glycans. Additionally, expression levels in transgenic plants are not high enough to lend itself to commercial production. (See, for example, U.S. Pat. No. 6,770,799 B2; see also, Evron et al., 2007). Similarly, low expression levels of 10-20 mg/kg of BChE in transgenic N. tabacum plants were also obtained (Rosenberg et al., unpublished data) indicating that higher levels of the ChE proteins were toxic to the plants and making that method unsuitable for commercial production.

Thus, there is a need for novel methods of making large amounts of cholinesterases for the detoxification and decontamination of organophosphorus compounds.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject.

The present inventors unexpectedly discovered that expressing a cholinesterase ("ChE") polynucleotide sequence with a tetramerization domain along with a proline-rich attachment domain (PRAD) of the rat Colq gene increases both the expression and thermal stability of ChE proteins. For example, expressing the E4-E6 AChE gene (Sternfeld et al., 1998) or the WT BChE genes containing a 40 amino acid tetramerization domain at the C-terminus with a PRAD sequence substantially and unexpectedly increases both expression and thermal stability of ChE proteins.

In preferred embodiments, a P19 gene is expressed along with ChE and PRAD to further enhance production of thermally stable ChE.

Other preferred embodiments include a targeting sequence on either the PRAD and/or the ChE sequence to direct proteins to specific cell compartments. Examples of such targeting sequence include, but are not limited to a SEKDEL (ser-glu-lys-asp-glu-leu), sequence (SEQ ID NO: 7), which allow for the retention in the endoplasmic reticulum (ER). In some embodiments the targeting sequence is located at either the N-terminal or C-terminal end. In preferred embodiments, the targeting sequence is located at the C-terminal end of either the PRAD and/or the ChE sequence.

Further embodiments include a Tag sequence on the ChE sequence. Examples of such Tag sequence included, but are not limited to a FLAG tag sequence. The Tag sequence can be located at either the N-terminal or C-terminal end and can be used for purification. In preferred embodiments, the Tag sequence is located at the C-terminal end.

Thus, the present invention relates to methods for the large-scale production of ChEs using expression systems and conditions designed to produce highly stable forms of ChEs. Preferably, the expression systems rely on a transient expression system, without the need for producing stable transfectants. In preferred embodiments, the expression systems can be produced in prokaryotic, mammalian, and/or plants systems, and in some circumstances, can be codon optimized for the particular expression system. These highly stable forms of ChEs can be used for a variety of uses, including in the detection, detoxification and decontamination of OPs.

In some aspects, the present invention relates to methods for the large-scale production of primate (preferably, for example, human and macaque) ChEs using transient expression systems without producing stable transfectants. More particularly, it relates to methods for the production of highly thermally stable forms of primate ChEs produced in mammalian and/or plant cells that can be used for the detection, detoxification and decontamination of OPs.

More specifically, the present invention relates to a method of producing a highly thermally stable ChE polypeptide, by transiently expressing a ChE polypeptide at least 70% identical to the polynucleotide sequence of SEQ ID NO:1-4 in a host cell, transiently expressing a PRAD polypeptide at least 70% identical to the polynucleotide sequence of the SEQ ID NO:5 in the host cell, collecting the extract comprising the ChE polypeptide, wherein said ChE polypeptide is highly thermally stable, for example, stable at least 40° C. for 8 hours and/or at 37° C. for 14 days. In a further preferred embodiment, a P19 polypeptide at least 70% identical to the polynucleotide sequence of SEQ ID NO:6 (FIG. 1) is also expressed along with ChE and PRAD to further enhance production of thermally stable ChE. Further, a KDEL sequence (SEQ ID NO: 8) may also be expressed along with the ChE polypeptide, the PRAD polypeptide, and/or the P19 polypeptide.

In a preferred embodiment, the ChE polypeptide is expressed transiently in a plant cell. In preferred embodiments, the plant cell is a *Nicotiana* plant species. In further preferred embodiments, the plant is *Nicotiana tabacum* SR1 (tobacco) or *Nicotiana benthamiana*. Plant cells, used according to the methods of the present invention are also specifically contemplated.

In further preferred embodiments, the polynucleotide sequences encoding the ChE is codon optimized for expression in plants. In further preferred embodiments, the ChE is codon optimized for tobacco plants.

The PRAD, ChE and/or the P19 sequence can be contained in the same or separate vectors. In one preferred embodiment, the polynucleotide sequences encoding the ChE sequence, the P19 sequence and/or the PRAD sequence are contained in three separate vectors. In another embodiment, the ChE sequence, the P19 sequence and/or the PRAD sequence are contained in two separate vectors. In another embodiment, the ChE sequence, the P19 sequence, and the PRAD sequence are contained in one vector.

Transient expression of the tetrameric forms of ChEs in plants can be achieved, for example, by transfection of *Nicotiana tabacum* and *Nicotiana benthamiana* species with plasmids containing said genes by *Agrobacterium* mediated-infiltration of the plants and/or leaves, followed by incubation of the leaves and/or plants and production of ChE-containing extract from the plant material.

The method of the present invention can also include the use of chitosan to produce said extract. In other preferred embodiments, the method of the present invention can also include the addition of collagen hydrolysate to said extract to increase thermal stability.

Methods of purification of ChE are also contemplated. For example, the ChE polypeptide can be purified using a column. Examples of such columns include a procainamide sepharose affinity chromatography column. Alternatively, the ChE polypeptide can be eluted with a buffer containing procainamide, decamethonium, acetylcholine, chlorine chloride, tetra methyl ammonium bromide or using salt gradients.

The ChE polypeptide produced by the method of the present invention is also contemplated. Preferably, the ChE polypeptide is obtained at an amount >400 mg/kg of leaf biomass. Alternatively, the ChE polypeptide is ~0.7% w/w in the prepared extract. In preferred embodiments, the ChE polypeptide is >98% pure (=~3,500 U/mg when purified). In further preferred embodiments, the ChE polypeptide is stable at 4-37° C. for >14 days in liquid form or lyophilized form. In even further preferred embodiments, the ChE polypeptide is stable for >8 hours at 40° C. and is still capable of functioning in a sensor for detecting OP on surfaces via irreversible inhibition of ChE catalytic activity at extreme temperatures of 50° C. and 0° C. Methods of using the ChE polypeptide produced by the described methods in detection, detoxification and/or decontamination of an organophosphorus compound are also contemplated.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

Embodiments are illustrated by way of example (and not limitation) in the figures of the accompanying drawings, in which like references, indicate similar elements and in which:

FIG. 1 shows the sequences of primate ChE molecules, PRAD and P19.

Figure 2:
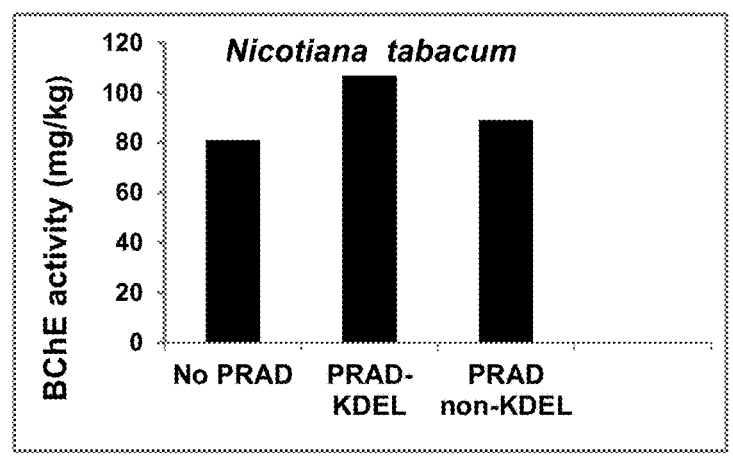
FIG. 2 is a graph depicting the expression of tetrameric forms of MaBChE-KDEL in *Nicotiana tabacum* SR1 in the presence of no-PRAD, PRAD-KDEL and PRAD-non-KDEL.
Figure 3:
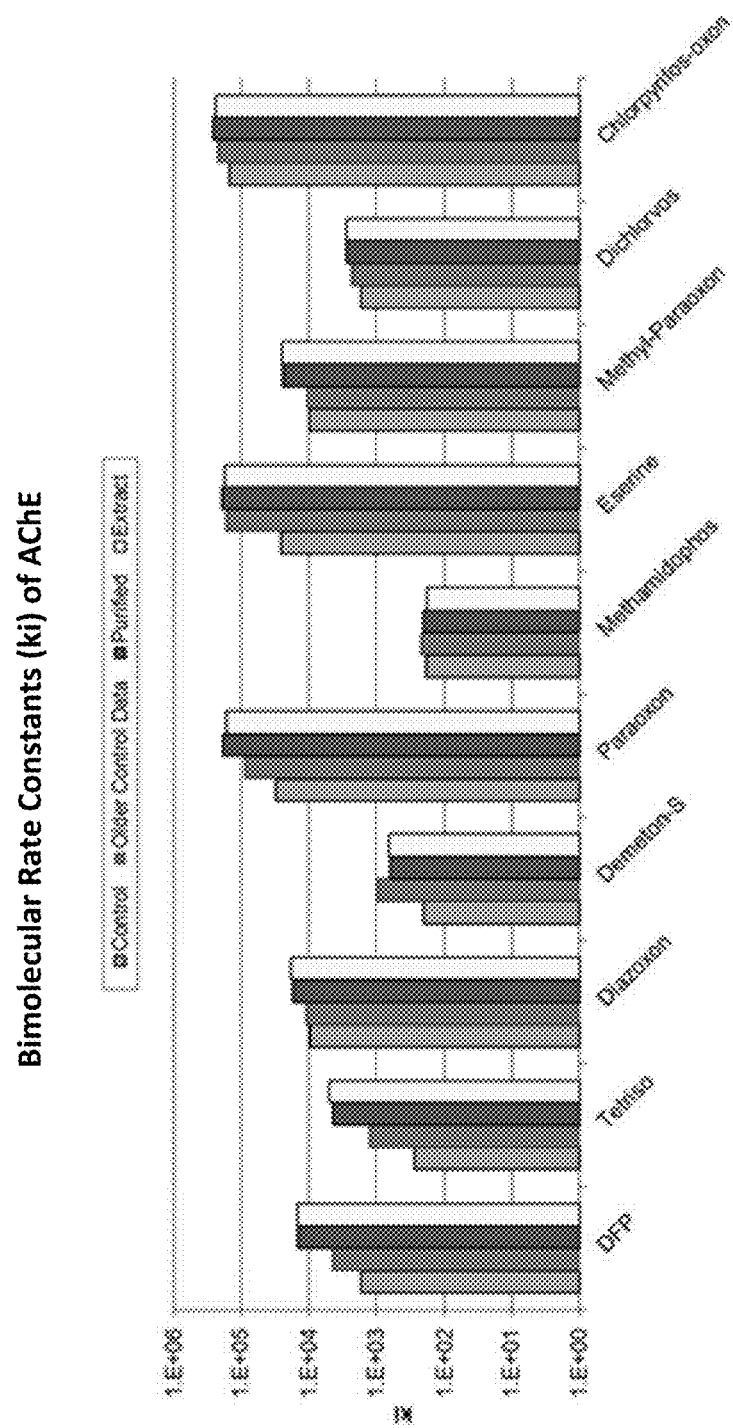
FIG. 3 is a graph depicting the pesticide inhibition profiles and bimolecular rate constants (ki) of the purified HuAChE and non-purified HuAChE-containing extracts compared with control AChE from another source (e.g., using a different process). First order rate constants for the inhibition of human AChE by various organophosphorus compounds. ki=−ln (inhibited rate/uninhibited rate)/inhibitor concentration (molar)/incubation time (minutes).

DETAILED DESCRIPTION OF THE INVENTION

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural nouns unless the content clearly dictates otherwise. For example, reference to "a polypeptide" includes a mixture of two or more such polypeptide molecules or a plurality of such polypeptide molecules. Similarly, reference to a "polynucleotide" includes a mixture of two or more such polynucleotide molecules or a plurality of such polynucleotide molecules.

As used herein, the term "comprise" or variations thereof such as "comprises" or "comprising" are to be read to indicate the inclusion of any recited integer (e.g., a feature, element, characteristic, property, method/process step or limitation) or group of integers (e.g., features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g., a feature, element, characteristic, property, method/process step or limitation) or group of integers (e.g., features, elements, characteristics, properties, method/process steps or limitations) alone. The invention will be described in more detail below.

A. Definitions

The technology described herein is directed to methods for the large-scale production of cholinesterases "ChEs" using systems designed to produce highly thermally stable forms of ChEs that are stable both in terms of thermal resistance and/or the duration of the resistance.

As used herein, "ChEs" refers to either class of proteins referred to as acetyl cholinesterase ("AChE") and/or butyrylcholinesterase ("BChE") and includes variants of those proteins as found in nature. The term "ChE", "AChE" and BChE" refer to the naturally derived protein sequence found in primates, preferably humans and macaque, as well as variants that have at least 70%, at least 75%, at least 80%, at least 85%, at least 90%, at least 95%, at least 96%, at least 97%, at least 98%, or at least 99% identity to the naturally derived amino acid sequence.

Both AChE and BChE are encoded by a single gene. In other preferred embodiments, the present invention provides a method for obtaining recombinant ChE which comprises the use of AChE DNAs (e.g., SEQ ID NO:1 (human) or SEQ ID NO:2 (macaque) or BChE sequences (SEQ ID NO:3 (human) or SEQ ID NO:4 (macaque)) which, in certain embodiments, can be codon optimized or may comprise different leader sequences for the particular expression system, for example, a plant expression system. In the case of AChE, alternative splicing, is known to generate different polypeptide isoforms with distinct C-termini. In one preferred embodiment, the present method relates to the production of the E4-E6 isoform of AChE (containing exons II, III, IV, VI) in which a truncated exon 4 is joined to exon 6 containing the tetramerization domain. In other embodiments, the BChE polypeptide includes exons II, III and IV with the tetramerization domain being in exon IV.

In the present invention, "PRAD" is defined as a gene encoding proteins/peptides capable of interacting with the C-terminal tetramerization domain of ChE monomers resulting in the formation of tetramers as well as the proteins/peptides encoded by the PRAD gene. Examples of such "PRAD" proteins/peptides are well known in the art and include, but are not limited to, peptides containing prolinerich-attachment domains e.g., the PRAD region of the rat Colq gene or the gene encoding the human lamellipodin proline rich peptides (Li et al., 2008). Other "PRAD" genes of the present invention include functionally equivalent genes found in different animal and plant species. Moreover, the definition of "PRAD" in the present invention not only includes the full length PRAD amino acid sequence, but also includes truncated forms and variants of PRAD that retain the ability to tetramerize ChE polypeptides of the present invention. For example, in another preferred embodiment, the invention relates to a method of increasing tetramerization and expression of ChE, wherein the method comprises the co-expression in the ER of a full-length ChE protein containing the 40 amino acid tetramerization domain and the KDEL tag at the C-terminus with the PRAD or the lamellipodin protein rich peptides also containing the KDEL tag. In this example, the increased expression presumably results from the rescue from degradation of the monomeric ChE chains in the ER by tetramerization peptides e.g., PRAD, lamellipodin and/or variations thereof. The invention specifically includes not only expressing the PRAD protein along with the ChE polypeptide of the invention, but also the direct addition of PRAD protein/peptides to an extract containing the ChE polypeptide.

In the present invention, "P19 gene" is defined as a plant viral-encoded suppressor of gene silencing. Thus in one preferred embodiment, the invention pertains to a process as herein described, wherein the method comprises the inclusion of a gene for the P19 plant viral-encoded suppressor of RNA silencing, for prolonging and increasing expression levels of human ChEs in plant cells, and preferably in Nicotiania species including N. benthamiana and N. tabacum. As used in the present invention, the "P19 gene" can be derived from any P19 gene, such as, for example, the Tombusvirus-based P19 genes, for example, from tomato bushy stunt virus (TBSV), cucumber necrosis virus (CNV), lettuce necrotic stunt virus (LNSV) (Garabagi et al., 2012), and/or an HC-Pro gene from turnip mosaic virus (TuMV). In addition, many non-P19 plant virus-derived genes known in the art with functional capabilities similar to P19 in many plant hosts have been described and can also be used in the present invention in the place of the P19 with the same result (Burgyan and Havelda, 2011); http://viralzone.expasy.org/all_by_species/891.html#tab6). Moreover, the definition of "P19" in the present invention not only includes the full length P19 amino acid sequence, but also includes truncated forms, derivatives, and variants of P19 that retain the ability to suppress gene silencing when used in the present invention.

In the present invention, a "targeting" sequence is defined as a peptide chain that directs the transport of a protein to a specific region in the cell, including the nucleus, mitochondria, endoplasmic reticulum (ER), chloroplast, apoplast, peroxisome and plasma membranes. Some target peptides are cleaved from the protein by signal peptidases after the proteins are transported. SEKDEL (ser-glu-lys-asp-glu-leu) (SEQ ID NO:7), or "KDEL" is just one preferred example of such an ER targeting sequence. Other examples of targeting sequence include, for example, mannose-6-phosphate which targets the lysosome. In further embodiments, the ChE sequences of the present invention further comprise a targeting sequence at either the N-terminal or the C-terminal end (e.g., KDEL) for retention in the ER where they undergo posttranslational modifications such as hydroxylation, disulfide bond formation, tetramerization and N-glycosylation in the ER. The targeting sequence of the present invention can be linked to either the PRAD and/or the ChE sequence of the present invention. In a preferred embodiment, ChE-KDEL and PRAD-KDEL sequences are used to both express ChEs at high levels and to produce different glycoforms to increase stability. In preferred embodiments, the targeting sequence is positioned at the C-terminal end.

In the present invention, a "Tag" sequence is well understood in the art as a sequence that can be used to purify a protein from the other, host cell proteins. A "HIS Tag" or "FLAG Tag" are examples of such a "Tag" sequence as is well known in the art. In some embodiments, the ChE and BChE polynucleotides further comprise polynucleotides encoding a Tag sequence. For example, the ChE and BChE polynucleotides may comprise a tag sequence at either the N-terminal or the C-terminal end to aid in purification. In preferred embodiments, the Tag sequence, is positioned at the C-terminal end of the PRAD and/or ChE polypeptide sequence to aid in purification. The Tag sequence of the present invention can be linked to either the PRAD and/or the ChE sequence of the present invention.

Thus, the present invention relates to a method of producing a highly thermally stable ChE polypeptide, by transiently expressing a polynucleotide sequence encoding a ChE polypeptide at least 70%, at least 75%, at least 80%, at least 85%, at least 90%, at least 95%, at least 96%, at least 97%, at least 98%, or at least 99% identity to the polynucleotide sequence of SEQ ID NO:1-4 in a host cell in the presence of a polynucleotide encoding a PRAD polypeptide at least 70%, at least 75%, at least 80%, at least 85%, at least 90%, at least 95%, at least 96%, at least 97%, at least 98%, or at least 99% identity to the polynucleotide sequence of SEQ ID NO:5. Further preferred embodiment includes also expressing a P19 polypeptide (SEQ ID NO:6) with or without KDEL sequence along with the ChE and/or PRAD polypeptide sequence.

In the present invention, a "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The terms "percent (%) sequence similarity", "percent (%) sequence identity", and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al, J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al, Nucleic Acids Res. 1997, 25:3389. Alternatively, PSI-Blast can be used to perform an iterated search that detects distant relationship between molecules. See Altschul et al., (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the World Wide Web.

Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the World Wide Web), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In the present invention, the term "highly thermally stable ChE" as either an extract or purified form is defined as stability at physiological temperatures for extended periods of time, and/or stability above and/or below physiological temperatures. Examples of such "highly thermally stable ChE" include, but are not limited to, (a) stability at least at 4° C., room temperature (RT) (e.g., 26° C.). for at least 14 days; or (b) stability at least at 37° C. for at least 14 days; or (c) stability at least at 40° C. for at least 8 hours; or (d) stability at least at 20-22° C. for at least 24 hours; or (e) capable of detecting OP on surfaces at extreme temperatures (such as at 50° C. and/or 0° C.); or (f) any combination thereof. Additionally, a "highly thermally stable ChE" can be stable at least at 70° C. For example, "a highly thermally stable ChE" may be stable at least at 70° C. for at least 2 weeks, for at least 3 weeks, for at least 4 weeks, for at least 5 weeks, or for at least 6 weeks. In a preferred embodiment, lyophilized ChE is stable at least at 70° C. for at least 6 weeks. In some instances, stability could be demonstrated following any combinations of (a) to (e), e.g., stability of lyophilized ChE at least at 70° C. followed by (c) and (e).

In the present invention, "isolated polypeptide" means the polypeptide is separated from its native environment and present in sufficient quantity to permit its identification or use. This means, for example, the polypeptide may be (i) selectively produced by expression cloning or (ii) purified as by chromatography or electrophoresis. Isolated proteins or polypeptides may be, but need not be, substantially pure. Because an isolated polypeptide may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in living systems, e.g., isolated from other proteins. Any of the peptides or polypeptides provided herein may be isolated.

In the present invention, "stable mutants" are defined as at least 1, at least 2, at least 3, at least 4, at least 5, at least 6, at least 7, at least 8, at least 9, at least 10 amino acid substitutions in AChE or BChE polypeptide sequence.

As used in the present application, "substitution" is an exchange of one amino acid for another at one or more sites within a ChE, PRAD, and/or a P19 sequence and may be designed to modulate one or more properties of the polypeptide, with or without the loss of other functions or properties. Substitutions may be "conservative", that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of a polypeptide or peptide is affected. Nonconservative changes typically involve substituting a residue with one that is chemically dissimilar, such as a polar or charged amino acid for a nonpolar or uncharged amino acid, and vice versa.

Preferably, the ChEs amino acid sequences of the present invention are mutated to increase stability. In further embodiments, the ChEs are mutated by the additions of asparagines. Specifically, the AChE sequences of the present invention are preferably mutated by the additions of asparagines to increase stability. In one embodiment, for the AChE protein, Aspartic acid (Asp) at position 61 and Serine (Ser) at position 541 were replaced with Asparagine (Asn) to enhance stability.

Substitutions include "deletions" of amino acids which are one or more amino acid residues removed from ChE, PRAD, and/or a P19 sequence. Individual residues can be deleted or a number of contiguous amino acids can be deleted. Preferably, the number of deleted amino acids of ChE, PRAD, and/or a P19 sequence are such that the resulting amino acid sequence is at least 5 amino acids, and more preferably at least 6 amino acids, and even more preferably at least 7 amino acids, and even more preferably at least 8 amino acids, and even more preferably at least 9 amino acids, and even more preferably at least 10 amino acids in length.

Of course, the number of amino acid substitutions a skilled artisan would make depends on many factors. In an additional preferred embodiment, the number of substitution for the amino acid sequence represented by ChE, PRAD, and/or a P19 sequence will be less than 6, 5, 4, 3, or 2 amino acids. Methods known in the art, such as site-directed mutagenesis or alanine-scanning mutagenesis (Cunningham and Wells, Science 244:1081-1085 (1989)) can be used to identify critical amino acids that cannot be modified in the ChE, PRAD, and/or P19 sequence. Additionally, structural analysis such as crystallization, nuclear magnetic resonance or photoaffinity labeling can also be used (Smith et al., J. Mol. Biol. 224:899-904 (1992) and de Vos et al., Science 255:306-312 (1992)).

B. Methods of Making Recombinant ChE

ChE polypeptides of the present invention may be made using recombinant techniques which are standard for one of skill in the art and can be used in the detection, detoxification and decontamination of OPs.

In such embodiments, a polynucleotide encoding the entire polypeptide sequence of the invention could be cloned into an expression vector that would be transcribed when transfected into a cell line or plant cell. In embodiments, an expression vector may comprise a plasmid, plant virus, retrovirus, or an adenovirus amongst others. The polynucleotide sequence can be isolated using standard molecular biology approaches, for example by using polymerase chain reactions to produce the polynucleotide, which is then purified and cloned into an expression vector and transfected into a cell line. Additional techniques useful in the practice of this invention may be found in Current Protocols in Molecular Biology 2007 by John Wiley and Sons, Inc.; Molecular Cloning: A Laboratory Manual (Third Edition) Joseph Sambrook, Peter MacCallum Cancer Institute, Melbourne, Australia; David Russell, University of Texas Southwestern Medical Center, Dallas, Cold Spring Harbor.

Selecting a particular polynucleotide of the present invention to encode a polypeptide of the invention is well within the skill in the art. For example, codon usage tables for a particular species may be used to generate a reverse complement that encodes a polypeptide of the present invention. See, for example, The Sequence Manipulation Suite: JavaScript programs for analyzing and formatting protein and DNA sequences. Biotechniques 28:1102-1104 (bioinformatics.org/sms2/rev_trans.html) or the Codon Usage Table: From the codon usage database (http://www.kazusa.or.jp/codon/): *Homo sapiens* [gbpri]: 93487 CDS's (40662582 codons). Alternatively, codon frequencies can be optimized for use in humans using frequency data such as that available from various codon usage records. One such record is the Codon Usage Database. Y. Nakamura et al., "Codon usage tabulated from the international DNA sequence databases: status for the year 2000." Nucl. Acids Res. 28, 292 (2000). Using these techniques, one skilled in the art readily can generate a "codon optimized" polynucleotide sequence that encodes a ChE, PRAD, and/or P19 sequence of the present invention.

In further embodiments, the polynucleotides can be operably joined to a promoter. Expression in prokaryotic hosts can be accomplished using prokaryotic regulatory regions. Expression in eukaryotic hosts can be accomplished using eukaryotic regulatory regions. Such regions will, in general, include a promoter region sufficient to direct the initiation of RNA synthesis. In embodiments, the nucleic acid can further comprise transcriptional and translational regulatory sequences, depending upon the nature of the host. The transcriptional and translational regulatory signals may be obtained or derived from viral sources, such as a retrovirus, adenovirus, bovine papilloma virus, simian virus, or the like.

In embodiments, a polynucleotide is inserted into a vector capable of integrating the desired sequences into the host cell chromosome. Additional elements may also be needed for optimal synthesis of the mRNA. These elements may include splice signals, as well as transcription promoters, enhancers, and termination signals and are all within the art.

Among vectors preferred for use in bacteria include pQE70, pQE60 and pQE-9, available from QIAGEN, Inc.; pBluescript™ vectors, Phagescript vectors, pNH8A, pNH16a, pNH18A, pNH46A, available from STRATAGENE™ Cloning Systems, Inc.; and ptrc99a, pKK223-3, pKK233-3, pDR540, pRIT5 available from PHARMACIA™ Biotech, Inc. Among preferred eukaryotic vectors are pWLNEO, pSV2CAT, pOG44, pXT1 and pSG available from STRATAGENE™; and pSVK3, pBPV, pMSG and pSVL available from PHARMACIA™. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PA0815 (all available from Invitrogen, Carlsbad, Calif.). Other suitable vectors will be readily apparent to the skilled artisan. Preferably, a polynucleotide is incorporated into a plasmid or viral vector capable of autonomous replication in the recipient host. Any of a wide variety of vectors may be employed for this purpose, such as prokaryotic and eukaryotic vectors. The eukaryotic vectors can be viral vectors. For example, and not by way of limitation, the vector can be a pox virus vector, herpes virus vector, adenovirus vector or any of a number of retrovirus vectors. The viral vectors include either DNA or RNA viruses to cause expression of the insert DNA or insert RNA. Alternatively, methods of introduction into the host cell can be performed by a variety of well-known methods, i.e., transformation, transfection, conjugation, protoplast fusion, electroporation, calcium phosphate-precipitation, direct microinjection, and the like. These techniques are all within the art. See, for example, Current Protocols in Molecular Biology 2007 by John Wiley and Sons, Inc.; Molecular Cloning: A Laboratory Manual (Third Edition) Joseph Sambrook, Peter MacCallum Cancer Institute, Melbourne, Australia; David Russell, University of Texas Southwestern Medical Center, Dallas, Cold Spring Harbor. Additionally, polynucleotides of the invention can be directly injected into cells or may be impelled through cell membranes after being adhered to microparticles or nanoparticles, such as the synthetic nanocarriers provided herein.

Recombinant production of the polypeptides of the invention may be produced in several ways using cells from different organisms, for example, animal cells, such as mammalian host cells (e.g., NSO, CHO, COS, 293, and Bowes melanoma cells), insect cells (e.g., for baculovirus expression, *Drosophila* S2 and *Spodoptera* Sf9 cells), bacterial cells, such as *E. coli, Streptomyces* and *Salmonella typhimurium* cells; fungal cells, such as yeast cells (e.g., *Saccharomyces cerevisiae* or *Pichia pastoris* (ATCCTM Accession No. 201178)); and plant cells. Appropriate culture mediums and conditions for the above-described host cells are known in the art.

Preferably, the expression systems rely on a transient expression system, without the need for producing stable transfectants. In preferred embodiments, the expression systems can be produced in prokaryotic, mammalian, and/or plants systems, and in some circumstances be codon optimized for the particular expression system.

Methods of transiently transfecting plant host cells, are well known in the art. In one preferred embodiment, transient expression in plant cells relies on either a non-*Agrobacterium*-mediated or an *Agrobacterium*-mediated gene delivery approach as is known in the art. In other embodiments, transient expression of plant cells include systems based on plant viruses to deliver the genetic information and combinations (e.g., Magnifection) as is also well known in the art.

In preferred embodiments, plasmids comprising sequence optimized ChEs are transiently transfected into either *Nicotiana tabacum* SR1 and *Nicotiana benthamiana* species by *Agrobacterium*-mediated infiltration. In some preferred embodiments, the method comprises the co-infiltration of the optimized or wild-type ChE gene with (i) the proline-rich attachment domain (PRAD) of the Colq gene for increasing the expression of tetrameric AChE and (ii) a P19 plant viral-encoded suppressor of gene silencing for prolonging and increasing expression levels of ChE in the plants. In some other embodiments, the method comprises the co-infiltration of the full-length AChE gene containing the 40 amino acid tetramerization domain at the C-terminus with the PRAD of the Colq gene for the expression of tetrameric form of AChE.

It is also specifically contemplated that any expression system of the present invention can transiently express the ChE polypeptide in a host cell where either the P19 and/or the PRAD genes are already stably transfected and incorporated into the host cell (e.g., either incorporation into the host genome or as an extrachromosomal plasmid). Similarly, the ChE polypeptide and/or the P19 and/or the PRAD gene can all be transiently transfected simultaneously or sequentially into the host cell.

In certain further embodiments, *Nicotiana tabacum* SR1 or *Nicotiana benthamiana* species are transfected with plasmids containing ChE-KDEL and/or the PRAD-KDEL sequences of the present invention by *Agrobacterium*-mediated infiltration to further increase the production of tetrameric ChE molecules (see FIG. 2).

In some embodiments, *Nicotiana tabacum* SR1 and *Nicotiana benthamiana* leaves, transfected with plasmids containing ChE-KDEL and/or PRAD-KDEL and or P19 sequences by *Agrobacterium*-mediated infiltration, may continue to express high levels of ChE proteins when maintained at 4° C. for 1-7 days.

One unexpected result of the present invention is that the levels of AChE proteins in the extracts produced by these expression systems and utilizing the said procedures are so high and stable that the extracts can be used for detection and detoxification without purification. Thus, based on similar AChE activity using the Ellman assay, the bimolecular rate constants of the extracts and the AChE purified by affinity chromatography of the extract were comparable (see FIG. 3).

For example, affinity chromatography can be used to separate the ChE away from other host proteins. For example, in preferred embodiments, affinity chromatography is conducted using a procainamide column to separate ChE proteins to >95% purity (pure protein containing 3,500 U/mg for Hu-AChE, 700 U/mg for HuBChE and 900 U/mg for MaBChE).

Alternatively, a ChE polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

In some embodiments, expression levels of ChEs produced in *N. tabacum* and *N. benthamiana* in the presence of PRAD, are in the range 100-140 mg/kg per leaf biomass. In other embodiments, the expression levels of tetrameric ChEs made in *N. benthamiana* co-infiltrated with P19, reach 900 mg/kg biomass. In some embodiments, processed leaf extracts contain AChE at 0.7% w/w. In other embodiments, affinity chromatography is conducted using passage over a procainamide column to purify ChE proteins to >95% purity (pure protein containing 3,500 U/mg for Hu-AChE, 700 U/mg for HuBChE and 900 U/mg for MaBChE). In other preferred embodiments, purified ChE proteins are obtained at >75% purity, >80% purity, >85% purity, >90% purity, >95% purity, >96% purity, >97% purity, >98% purity, >99% purity, and/or at 100% purity.

In one preferred embodiment, chitosan can be used in the processing of the leaf extract to clarify plant extracts. In a further preferred embodiment, collagen is added to the leaf extract and purified ChE to even further increase thermal stability and shelf life at extreme temperatures.

In other embodiments, the unpurified extract is >80% functionally active in tests conducted at 40° C. for 8 hours. In other embodiments, the formulated ChE extract and/or the purified ChE, is functionally active in detection assays using 0.1 ug OP after 8 hours at 40° C., after 24 hours at 20-22° C. and for 5 minutes at 50° C. and 0° C.

In other embodiments, purified ChE is stable at 37° C. for >14 days (FIG. 4).

In some embodiments the ChE extracts or purified forms are maintained in a liquid, frozen or powdered form.

Moreover, the invention additionally encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH.sub.4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein or use as a diagnostic.

Figure 5:
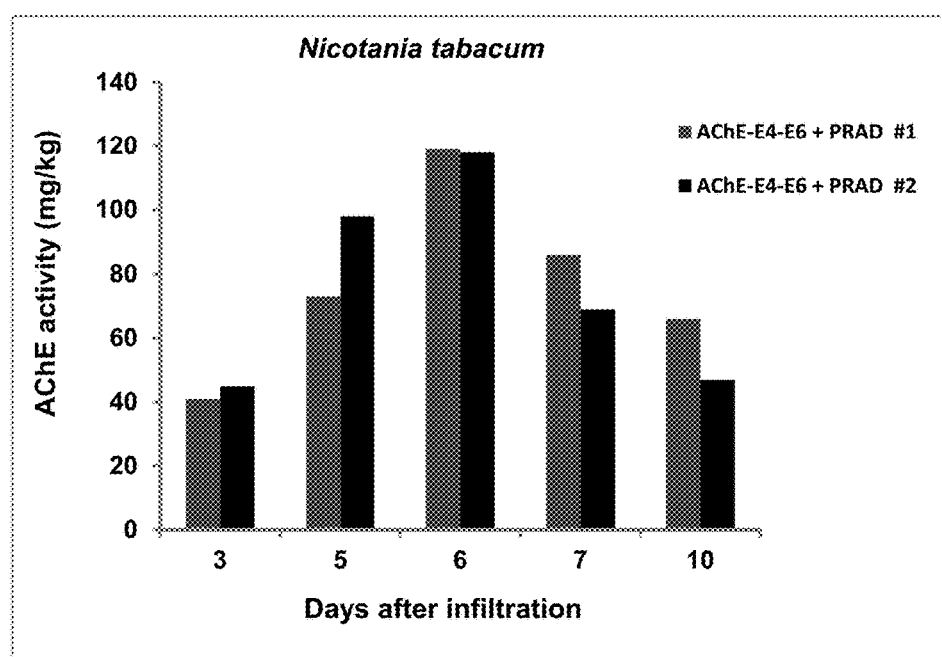
FIG. 5 is a graph depicting the expression of tetrameric forms of HuAChE-E4-E6-KDEL in two different *Nicotiana tabacum* SR1 plants the presence of PRAD-KDEL.
Figure 6:
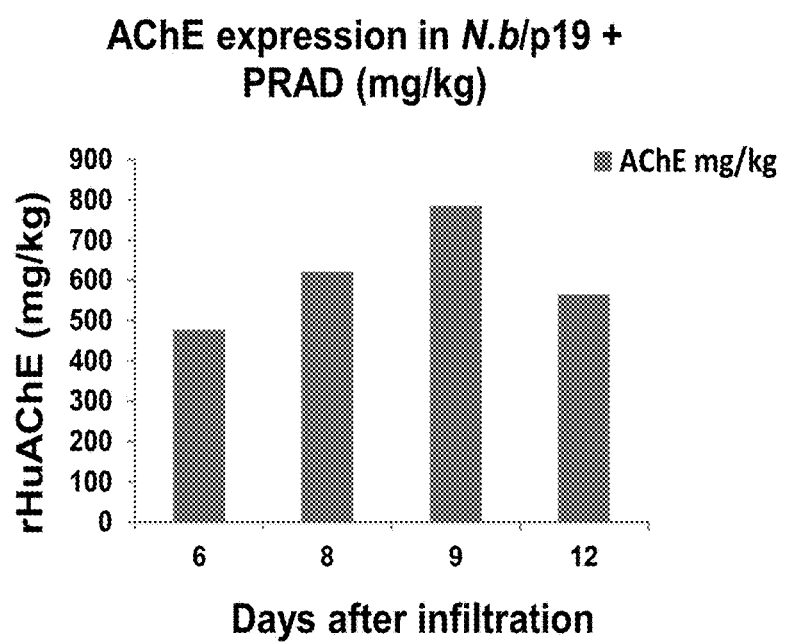
FIG. 6 is a graph depicting the expression of tetrameric forms of HuAChE-E4-E6-KDEL in *Nicotiana benthamiana* in the presence of PRAD-KDEL and P19.
Figure 7:
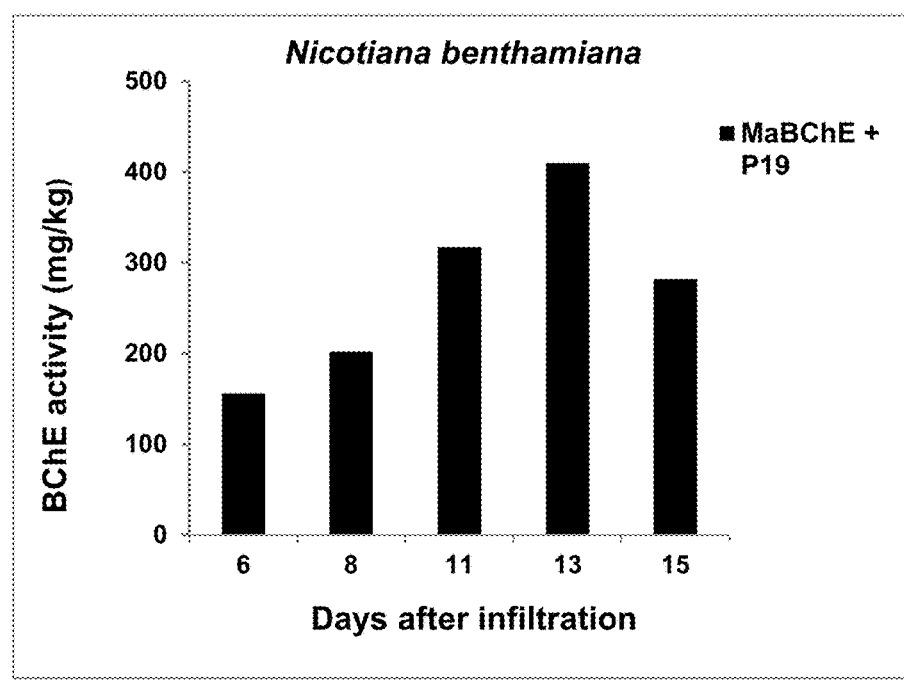
FIG. 7 is a graph depicting the expression of tetrameric forms of MaBChE-KDEL in *Nicotiana benthamiana* in the presence of P19.

*Nicotiana* plant species, including tobacco, have been identified as a cost-effective means for the expression of large quantities of recombinant human AChE (FIGS. 5-6). In contrast to transgenic systems, tetrameric forms of AChE and BChE can be produced transiently at high levels in at least two *Nicotiana* plant species (FIGS. 5-7). The tetrameric form of AChE is produced by co-expression of full-length AChE gene in the presence and/or absence of PRAD and P19; expression levels reaching >900 mg/kg in *Nicotiana benthamiana* peaked on day 9-14 (FIG. 6), while expression levels of 100-140 mg/kg in *Nicotiana tabacum* SR1 peaked on day 5-7 in the presence of PRAD (FIG. 5). Although, the expression of tetrameric AChE and BChE is favored in *Nicotiana benthamiana*, containing the P19 gene, both tetrameric ChEs are expressed at similar levels in *Nicotiana tabacum* SR1 in the presence of PRAD with no P19. While *Nicotiana benthamiana* may be the best system for the expression of AChE in terms of amount, these plants will currently have to be grown in the greenhouse. On the other hand, *Nicotiana tabacum* SR1 is a larger plant and can potentially be grown in the field resulting in a lower cost/kg of leaf biomass

C. Method of Using the Thermally Stable Form of ChE

In some embodiments, the present invention provides a method for in vitro detection, detoxification and decontamination of organophosphorus compounds which comprises using the ChE preparation made according to the method described above.

As well as their use of ChEs as stoichiometric OP bioscavengers for an in vivo treatment, thermally-stable ChEs could also be used for a dialysis-like device as well as in a cream or gel that could be applied to the skin and bind nerve agents and remove them from the skin before they can penetrate the skin and enter the bloodstream.

In addition to their use as a therapeutic human pretreatment, cholinesterases such as ChEs are being evaluated for their effectiveness in enzyme-based detection and decontamination/neutralization/clean-up technologies for remediation purposes following any accidental or deliberate terrorist release of chemical warfare agent (CWA). In this context, several enzyme-based products are being developed for neutralization/cleanup following release in a building or transportation hub: DEFENZ™ VX-G (for decontamination of VX and G-type nerve agents) and DEFENZ™ B-HD (for decontamination of sulfur mustard [HD]). In addition, the extent to which the efficacy of the enzyme solutions changed after preparation and storage was evaluated. DEFENZ™ VX-G contains granulated organophosphorus acid anhydrolase (OPAA) and organophosphorus hydrolase (OPH) enzymes while DEFENZ™ B-HD contains an arylesterase enzyme that catalyzes a chemical reaction to produce peracetic acid.

Thus, novel methods of production of highly stable ChE's at high levels are required for detoxification and decontamination of organophosphorus compounds; including ChEs for sensors and devices capable of detecting/identifying nerve agents and OP pesticides on surfaces, in water samples, and in air. A more thermally stable version of ChE can be used as a catalytic reporter for detection of nerve agents on hot surfaces and at elevated temperatures where physiologically active AChE alone would denature and not persist for sufficient time to complete decontamination. Thermally stable ChEs, could also be utilized in field-portable diagnostic assays, and in sensors that can be used to determine the location of chemical agents on surfaces with the intent to decontaminate the surface. To meet this need, we have therefore developed a form of ChE that is highly stable at temperatures exceeding 37° C. for long periods. Additionally, the sensors can be stored after production, but prior to use, for extend periods at temperatures exceeding 37° C. To be used to detect an OP compound after being stored, the enzyme should retain most of the activity of the original enzyme when formulated in the sensor.

Figure 4:
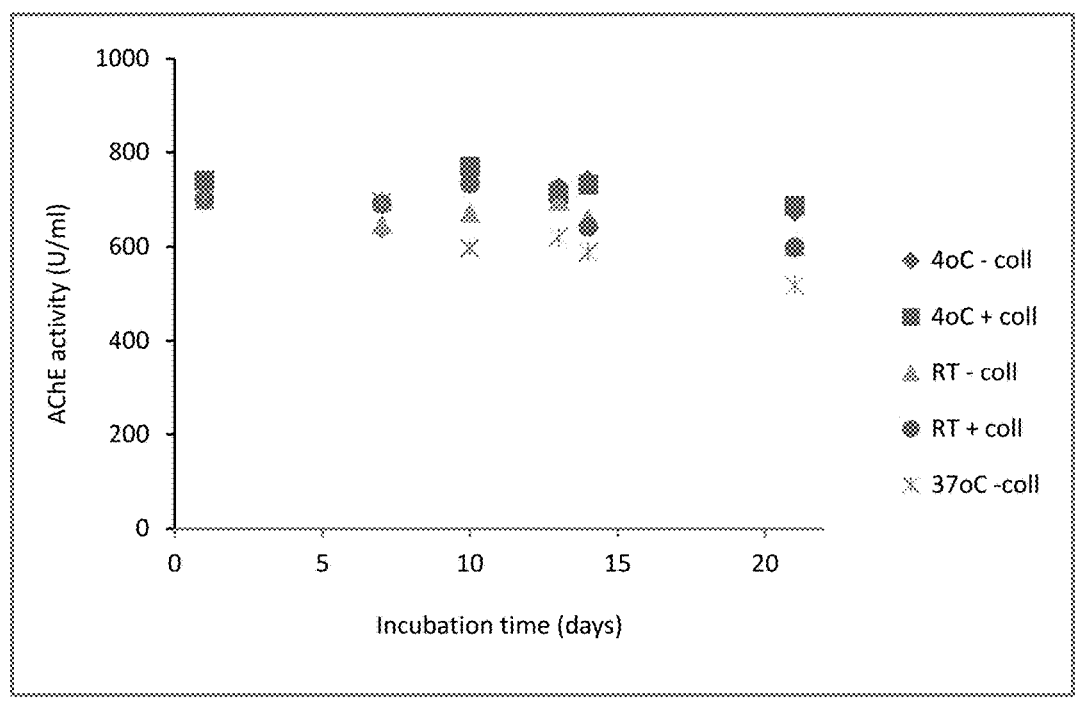
FIG. 4 is a graph depicting the thermal stability, measured in days, of purified human AChE stored at 4° C., RT and 37° C. in liquid form with and without collagen.

The thermal stability of this enzyme has been determined in liquid form and freeze-dried forms. The enzyme activity was stable when stored in liquid form at 4° C., 26° C. and 37° C. for at least 14 days with or without addition of a molecular stabilizer, such as a sugar, protein digest, or other stabilizer known in the art for lyophilization excipients (FIG. 4). In addition, formulated liquid or freeze-dried preparations of plant expressed AChE exhibit little loss of activity and are stable at 40° C. for 8 hours or at 20-22° C. for 24 hours with or without addition of a molecular stabilizer, such as a sugar, protein digest, or other stabilizer known in the art for lyophilization excipients.

Sensors utilizing recombinant human AChE expressed in *Nicotiana* in various forms were evaluated for their performance at extreme temperatures. In one embodiment, a colorimetric spray containing AChE was applied to surfaces at temperatures of either 0° C. or 50° C. A control tile and a tile containing 1 milligram of an organophosphorus pesticide, paraoxon, were sprayed with the sensor. On the clean surface, the sensor demonstrated no response and it remained the original yellow color, which indicates that the AChE remains catalytically active. On the plates containing the paraoxon challenge, the AChE enzyme was inhibited by the paraoxon, causing the gradual development of a localized red spot on the surface. This red color indicates that the enzyme was inhibited by the paraoxon and that a proper response was achieved.

These tests were executed both with freshly prepared sprays containing recombinant human AChE from *Nicotiana*, and were repeated again after the formulation was stored continuously for 8 hours at 40° C. In each case, the sensors responded appropriately, indicating that the recombinant human AChE is catalytically active and thermally stable at elevated temperatures both in liquid solution, and when applied to hot surfaces, for extended periods of time which significantly exceed anything that has been reported in literature to date.

Human ChEs produced in plants as detection, detoxification and decontamination agents have the advantage of high expression levels, high thermal stability and in some cases, the ability to use extracts obviating the requirement for expensive purification procedures.

EXAMPLES

Example 1. Production of Plant/Leaf Extract

One liter of a modified extraction buffer containing 5 mM $MgCl_2$, 4 mM DTT, 150 mM sodium metabisulfite and 10% sucrose in PBS pH 7.4 was prepared and chilled at 4° C. before use. Chitosan was prepared (Chitosan, low molecular weight, Sigma Aldrich 448869-50 g) by adding 1% w/v chitosan into 1% acetic acid and the solution stirred for at least 30 minutes until dissolved and taking on a gelatinous looking appearance. Frozen leaves were ground in a Vitamix blender with 5× w/v extraction buffer. After grinding, the slurry was passed through Miracloth (Calbiochem #475855), poured into centrifuge bottles and centrifuged at 20,000×g for 15 minutes. After centrifugation, the supernatant was poured into a beaker, pH changed to 7.4 and chitosan added at 0.2% v/v. The extract containing chitosan was then stirred at 4° C. for 30 minutes, removed from the stirrer, and left for an additional 30 minutes at 4° C. The extract was poured into centrifuge bottles and centrifuged at 1500 rpm in a refrigerated Sorvall RT6000 at 4° C. for 5 minutes. Supernatant was decanted and left at 4° C. until ChE level was determined. In some cases, collagen hydrolysate was added to the extract prior to it being aliquoted and frozen at −20° C.

AChE and BChE activity was determined spectrophotometrically at 25° C. according to the Ellman method. See Ellman et al., 1961, which is herein incorporated by reference. The assay mixture contained 1 mM aceylthiocholine as the substrate and 1 mM 5,5-dithiobisnitrobenzoic acid (DTNB) in 50 mM sodium phosphate, pH 8.0. at room temperature (RT). In assays using mammalian cells, 20 uM ethopropazine was used as a BChE-specific inhibitor. BChE activity was assessed using 1 mM butyrylthiocholine (BTC) as substrate and 0.5 mM 5,5-dithiobis 2-nitrobenzoic acid (DTNB). The formation of product was followed by monitoring the increase in absorbance of 5-thio-2-nitrobenzoic acid at 412 nm using a molar extinction coefficient of 13,600M−1 [26]. One unit of the enzyme activity is defined as the amount required to hydrolyze 1 μmol of substrate/min.

In many cases, transient plant expression generates extracts that contain sufficient ChE activity that purification was not needed for purposes of detection and decontamination of OPs. Recombinant AChE and BChE in supernatants (SN) or extracts are purified using procainamide sepharose chromatography as described previously (De la Hoz et al., 1986). After loading the SN or extract and washing the column, BChE is generally eluted with a 0.1-1M NaCl gradient but both AChE and BChE can be efficiently eluted using either 0.2M procainamide, 0.2M acetylcholine, 0.02M decamethodium, 0.5M chlorine chloride or 0.5M tetra methyl ammonium bromide.

Example 2. Physical Properties

In vitro stability of the human ChE preparations at different storage temperatures was examined Aliquots of the purified human AChE preparations in liquid form (1 in 50 mM sodium phosphate, pH 8.0+10% glycol+1 mM EDTA) were stored at 4° C., 25° C. and 37° C.; aliquots were removed at various time intervals over 21 days and assayed for AChE activity using the Ellman assay known in the art. The activity of human AChE preparations were found to be stable 4° C., 25° C., 37° C. for at least 14 days and still >70% functional after 21 days as shown in FIG. 4.

Pesticide Inhibition Profiles were assessed to demonstrate AChE produced in *Nicotiana* plants displayed similar inhibition profiles to current sources of human AChE by a panel of cholinesterase OP inhibitors. AChE-containing plant extracts and purified plant AChE were diluted to rate of 250-300 mOD/min in Ellman assay, incubated 10 minutes with various inhibitors ranging from 100 pM to 1 mM in isopropanol and the biomolecular rate constant ($k_i$) were calculated based on ratio of inhibited rate to uninhibited rate. The results (FIG. 1) were within acceptable deviation of compared to current control AChE preparations.

Sensors utilizing various forms of *N. bentamiana*-derived HuAChE were evaluated for their performance at extreme temperatures. In one embodiment, a colorimetric spray containing AChE was applied to surfaces with either 0° C. or 50° C. temperatures. A control tile and a tile containing 1 milligram of an organophosphorus pesticide, paraoxon, were sprayed with the sensor. On the clean surface, the sensor demonstrated no response and it remained the original yellow color, which indicates that the AChE remains catalytically active. On the plates containing the paraoxon challenge, the AChE enzyme was inhibited by the paraoxon, causing the gradual development of a localized red spot on the surface. This red color indicates that the enzyme was inhibited by the paraoxon and that a proper response was achieved.

Tests were also executed both with freshly prepared sprays containing HuAChE extracts and in a purified form, after the formulation was stored continuously for 8 hours at 40° C. or 24° C. at RT. In each case, the sensors responded appropriately, indicating that the recombinant human AChE is catalytically active and thermally stable at elevated temperatures both in liquid solution, and when applied to hot surfaces, for extended periods of time which significantly exceed anything that has been reported in literature to date. In certain tests, the high stability of the *Nicotiana benthamiana*-derived AChE could be further enhanced by the addition of collagen hydrolysate.

The stability of the human AChE preparations at different storage temperatures was examined. Aliquots of the human AChE preparations in liquid extract and purified forms in 50 mM sodium phosphate, pH 8.0+10% glycerol+1 mM EDTA) were stored at 4° C., 25° C. and 37° C.; aliquots were removed at various time intervals over 21 days and assayed for AChE activity using the Ellman assay known in the art. The activity of human AChE preparations were found to be stable at 4° C., 25° C., 37° C. for at least 12 days as shown in FIG. 4. In addition, formulated liquid or freeze-dried preparations of plant expressed AChE was stable at 40° C. for 8 hours or at 20-22° C. for 24 hours.

As provided herein, the human AChE preparations of the present invention may be used as a detection, detoxification and decontamination agent against multiple $LD_{50}$'s of a wide variety of potent OP agents.

As disclosed herein, the present invention provides a process for the large-scale manufacture of highly stable recombinant human AChE. Tetrameric forms of primate AChE and BChE can be expressed transiently at high levels in two *Nicotiana* plant species. The tetrameric form of AChE is produced by co-expression of full-length AChE gene in the presence and absence of PRAD and P19; expression levels of >400 mg/kg in *Nicotiana benthamiana* peaked on day 12-14, while expression levels of >120 mg/kg in *Nicotiana tabacum* SR1 in the presence of PRAD peaked on day 5-6. Although, the expression of tetrameric AChE is favored in *Nicotiana benthamiana* in the presence of P19, tetrameric AChE is expressed at similar levels in *Nicotiana tabacum* SR1 in the absence of P19. The expressed enzymes can be purified from leaf extract reaching least 40-50% purity following one passage over a procainamide affinity column. The yield, purity and thermal stability met or exceeded expectations for detection, decontaminant and detoxicant of OPs. Based on the successful results of this study, a manufacturing procedure has been developed that is suitable for the large-scale production of highly stable human AChE for application as a decontaminant of OP-exposed surfaces above and below physiological temperature.

REFERENCES

Hardison L S Jr, Wright E, Pizon A F. Phosgene Exposure: A Case of Accidental Industrial Exposure. J Med Toxicol. 2013; [Epub ahead of print].

Sidell, F R, Takafuji, E T, Franz, D R. Medical aspects of chemical and biological warfare. Borden Institute, Walter Reed Army Medical Center. 1997; pp. 147-149.

Bonner M R, Coble J, Blair A et al. "Malathion Exposure and the Incidence of Cancer in the Agricultural Health Study". American Journal of Epidemiology 2007; 166 (9): 1023-34.

Buckley, N A, Roberts, D, Eddleston, M. (2004) "Overcoming apathy in research on organophosphate poisoning", BMJ 329:1231-1233.

Ashani Y, Shapira S, Levy D, Wolfe A D, Doctor B P, Raveh L. Butyrylcholinesterase and acetylcholinesterase prophylaxis against soman poisoning in mice. Biochem Pharmacol 1991; 41:37-41.

Raveh L, Grunwald J, Marcus D, Papier Y, Cohen E, Ashani Y Human butyrylcholinesterase as a general prophylactic antidote for nerve agent toxicity. In vitro and in vivo quantitative characterization. Biochem Pharmacol 1993; 45:2465-74.

Brandeis R, Raveh L, Grunwald J, Cohen E, Ashani Y Prevention of soman-induced cognitive deficits by pretreatment with human butyrylcholinesterase in rats. Pharmacol Biochem Behav 1993; 46:889-96.

Raveh L, Grauer E, Grunwald J, Cohen E, Ashani Y The stoichiometry of protection against soman and VX toxicity in monkeys pretreated with human butyrylcholinesterase. Toxicol Appl Pharmacol 1997; 145:43-53.

Ashani Y. Prospective of human butyrylcholinesterase as a detoxifying antidote and potential regulator of controlled-release drugs. Drug Dev Res 2000; 50:298-308.

Saxena A, Sun W, Fedorko J M, Koplovitz I, Doctor B P. Prophylaxis with human serum butyrylcholinesterase protects guinea pigs exposed to multiple lethal doses of soman or VX. Biochem Pharmacol 2011; 81:164-9.

Lenz D E, Maxwell D M, Koplovitz I, Clark C R, Capacio B R, Cerasoli D M, et al. Protection against soman or VX poisoning by human butyrylcholinesterase in guinea pigs and cynomolgus monkeys. Chemico-Biological Interactions 2005; 157-158:205-10.

Sun W, Doctor B P, Lenz D E, Saxena A. Long-term effects of human butyrylcholinesterase pretreatment followed by acute soman challenge in cynomolgus monkeys. Chemico-biological interactions 2008; 175:428-30.

Allon N, Raveh L, Gilat E, Cohen E, Grunwald J, Ashani Y. Prophylaxis against soman inhalation toxicity in guinea pigs by pretreatment alone with human serum butyrylcholinesterase. Toxicol Sci 1998; 43:121-8.

Saxena A, Sun W, Dabisch P A, Hulet S W, Hastings N B, Jakubowski E M, et al. Pretreatment with human serum butyrylcholinesterase alone prevents cardiac abnormalities, seizures, and death in Göttingen minipigs exposed to sarin vapor. Biochem Pharmacol. 2011; 82(12):1984-93.

Y. J. Rosenberg Y J, Laube B, Maoo L J, X. M. Jiang X M, Hernandez-Abanto S, Lee K D, Adams R. Pulmonary delivery of an aerosolized recombinant human butyrylcholinesterase pretreatment protects against aerosolized paraoxon in macaques, Chem. Biol. Interact. 2013; 2013: 167-171.

Fischer M, Ittah A, Liefer I, Gorecki M. Expression and reconstitution of biologically active human acetylcholinesterase from *Escherichia coli*. Cell Mol Neurobiol. 1993; 13:25-38.

Kronman C, Velan B, Gozes Y, Leitner M, Flashner Y, Lazar A, Marcus D, Sery T, Papier Y, Grosfeld H, et al. Production and secretion of high levels of recombinant human acetylcholinesterase in cultured cell lines: microheterogeneity of the catalytic subunit. Gene. 1992; 121: 295-304.

Chilukuri N, Parikh K, Sun W, Naik R, Tipparaju P, Doctor B P, Saxena A. Polyethylene glycosylation prolongs the circulatory stability of recombinant human butyrylcholinesterase. Chem Biol Interact. 2005; 157-158:115-21.

Rosenberg Y J, Saxena, A, Sun W, Jiang X M, Chilukuri N, Luo C, Doctor B P, Lee K D. Demonstration of in vivo stability and lack of immunogenicity of a polyethyleneglycol-conjugated recombinant CHO-derived butyrylcholinesterase bioscavenger r using a homologous macaque model, Chem. Biol. Interact. 2010; 187:279-286.

Huang Y J, Huang Y, Baldassarre H, Wang B, Lazaris A, Leduc M et al. Recombinant human butyrylcholinesterase from milk of transgenic animals to protect against organophosphate poisoning. Proc Natl Acad Sci USA. 2007; 104(34):13603-8.

Evron T, Geyer B C, Cherni I, Muralidharan M, Kilbourne J, Fletcher S P, Soreq H, Mor T S. Plant-derived human acetylcholinesterase-R provides protection from lethal organophosphate poisoning and its chronic aftermath. FASEB J. 2007; 21(11):2961-9.

Li H, Schopfer L M, Masson P, Lockridge O. Lamellipodin proline rich peptides associated with native plasma butyrylcholinesterase tetramers. Biochem J. 2008; 411: 425-32.

Sternfeld M, Ming G, Song H, Sela K, Timberg R T, Poo M, Soreq H.1 Acetylcholinesterase enhances neurite growth and synapse development through alternative contributions of its hydrolytic capacity, core protein, and variable c termini. J Neurosci. 1998; 18:1240-1249.

Garabagi F, Gilbert E, Loos A, McLean M D, Hall J C. Utility of the P19 suppressor of gene-silencing protein for production of therapeutic antibodies in *Nicotiana* expression hosts. Plant Biotechnol J. 2012 December; 10(9): 1118-28.

Burgyan J, Havelda, Z. 2011. Viral suppressors of RNA silencing. Trends Plant Sci 16(5): 265-272.

Ellman G L, Courtney K D, Andres Jr V, Feather-stone R M. A new and rapid colorimetric determination of acetylcholinesterase activity. Biochem. Pharmacol. 1961; 7:88-95 Life Sci. 1986 Jul. 21; 39(3):195-9.

De la Hoz D, Doctor B P, Ralston J S, Rush R S, Wolfe A D. A simplified procedure for the purification of large quantities of fetal bovine serum acetylcholinesterase. Life Sci. 1986; 39:195-9.

What is claimed:

1. A method for the large-scale production of a ChE protein in a plant extract, wherein said method comprises:
   (a) expressing a ChE polypeptide in a plant cell, wherein said plant cell comprises a ChE encoding polynucleotide of SEQ ID NO:1, a PRAD encoding polynucleotide of SEQ ID NO:5, and a P19 encoding polynucleotide;
   (b) generating a plant extract;
   (c) adding chitosan to said plant extract;
   (d) recovering said plant extract comprising said CheE polypeptide,
   wherein said ChE polypeptide in said plant extract retains >70% enzymatic activity at 4° C. for at least 14 days and wherein ChE polypeptide is obtained at an amount >200 mg/kg of leaf biomass.

2. The method of claim 1, wherein the ChE polypeptide in said plant extract retains >70% enzymatic activity at 25° C. for at least 14 days.

3. The method of claim 1, wherein the ChE polypeptide in said plant extract retains >70% enzymatic activity at 37° C. for at least 14 days.

4. The method of claim 1, wherein the ChE polypeptide in said plant extract retains >80% enzymatic activity at 40° C. for 8 hours.

5. The method of claim 1, wherein the P19 encoding polynucleotide is polynucleotide sequence of SEQ ID NO:6.

6. The method of claim 1, wherein the PRAD encoding polynucleotide is stably expressed.

7. The method of claim 6, wherein the P19 encoding polynucleotide is stably expressed.

8. The method of claim 1, wherein the encoded ChE and PRAD polypeptides are transiently expressed in the plant cell.

9. The method of claim 8, wherein the P19 encoding polynucleotide is stably expressed.

10. The method of claim 1, wherein the encoded ChE, PRAD, and P19 polypeptides are transiently expressed in the plant cell.

11. The method of claim 1, wherein the ChE encoding polynucleotide and/or the PRAD encoding polynucleotide further comprises a polynucleotide encoding a targeting sequence.

12. The method of claim 11, wherein the targeting sequence is a KDEL sequence.

13. The method of claim 11, wherein the targeting sequence is at the C-terminus of the ChE and/or PRAD encoding polynucleotides.

14. The method of claim 1, wherein the ChE encoding polynucleotide further comprises a polynucleotide encoding a Tag sequence.

15. The method of claim 1, wherein the plant cell is a member of the Solanaceae family.

16. The method of claim 1, wherein the plant cell is a tobacco plant.

17. The method of claim 1, wherein the plant cell is a member of the *Nicotiana* genus.

18. The method of claim 17, wherein the plant cell is *Nicotiana benthamiana* or *Nicotiana tabacum*.

19. The method of claim 1, wherein the ChE encoding polynucleotide and/or the PRAD encoding polynucleotide and/or the P19 encoding polynucleotide is codon optimized for expression in plants.

20. The method of claim 19, wherein the ChE, PRAD, and/or the P19 encoding polynucleotides are codon optimized for expression in tobacco plants.

21. The method of claim 1, wherein the ChE, PRAD, or P19 encoding polynucleotides are contained in three separate vectors.

22. The method of claim 1, wherein the ChE, PRAD, or P19 encoding polynucleotides are contained in two separate vectors.

23. The method of claim 1, wherein the ChE, PRAD, and P19 encoding polynucleotides are contained in one vector.

24. The method of claim 1, wherein said method further comprises the addition of collagen to said step (c).

25. The method of claim 1, wherein said method further comprises purifying said ChE polypeptide from said plant extract.

26. The method of claim 24, wherein said ChE polypeptide is purified using a column.

27. The method of claim 26, wherein said column is a procainamide sepharose affinity chromatography column.

28. The method of claim 27, wherein said ChE polypeptide is eluted from said column with a buffer containing procainamide, decamethonium or acetylcholine, chlorine chloride, tetra methyl ammonium bromide or a salt gradient.

29. The plant extract comprising the ChE polypeptide produced by the method of claim 1.

30. The plant extract comprising the ChE polypeptide produced by the method of claim 2.

31. The plant extract comprising the ChE polypeptide produced by the method of claim 3.

32. The plant extract comprising the ChE polypeptide produced by the method of claim 4.

33. The plant extract comprising the ChE polypeptide produced by the method of claim 1, wherein said ChE polypeptide is stable:
   a. at least 20-22° C. for at least 24 hours;
   b. at least 70° C. as a lyophilized form for at least 2 weeks;
   c. at least 70° C. as a lyophilized form for at least 3 weeks;
   d. at least 70° C. as a lyophilized form for at least 4 weeks;
   e. at least 70° C. as a lyophilized form for at least 5 weeks;
   f. at least 70° C. as a lyophilized form for at least 6 weeks; and
   g. capable of detecting OP on surfaces at extreme temperatures (such as at 50° C. and/or 0° C.).

34. The plant extract comprising the ChE polypeptide of claim 29, wherein said plant extract is a powder, liquid, or freeze-dried formulation.

35. A plant cell used in the method of claim 1.

36. The plant cell of claim 35, wherein the plant cell is a member of the Solanaceae family.

37. The plant cell of claim 35, wherein the plant cell is a tobacco plant.

38. The plant cell of claim 35, wherein the plant cell is a member of the *Nicotiana* genus.

39. The plant cell of claim 38, wherein the plant cell is *Nicotiana benthamiana* or *Nicotiana tabacum*.

40. A method of detection, detoxification and/or decontamination of an organophosphorus compound comprising: applying the plant extract comprising said ChE polypeptide of claim 1 to a surface to detect, detoxify and/or decontaminate an organophosphorus compound.

41. The method of claim 40, wherein the detection, detoxification and/or decontamination occurs on a solid surface.

42. The method of claim 41, wherein the solid surface is at or above physiological temperature.

43. The method of claim 42, wherein the solid surface is at temperatures above 80° F.

44. The method of claim 41, wherein the solid surface is below physiological temperature.

45. The method of claim 40, wherein the surface comprises a liquid droplet.

46. The method of claim 40, wherein the surface is an exposed dry surface.

* * * * *

SEQUENCE LISTING

<160> NUMBER OF SEQ ID NOS: 8

<210> SEQ ID NO 1
<211> LENGTH: 1845
<212> TYPE: DNA
<213> ORGANISM: Homo sapiens

<400> SEQUENCE: 1

| | | | | | | |
|---|---|---|---|---|---|---|
| atgaggcctc | ctcagtgcct | tcttcacact | ccatctcttg | ctagtccttt | gttgctcttg | 60 |
| cttctttggc | ttctcggagg | tggtgttgga | gctgaaggta | gagaagatgc | tgagcttctt | 120 |
| gttactgtta | gaggcggccg | cttgagggga | attagactta | agactccagg | tggcccagtg | 180 |
| tctgctttcc | ttggtattcc | atttgctgaa | ccacccatgg | gcccaagaag | atttcttcca | 240 |
| ccagaaccta | agcagccttg | gtctggtgtt | gtgaacgcta | ctactttcca | gtccgtgtgc | 300 |
| taccagtatg | tggatactct | ctacccagga | ttcgagggca | ctgagatgtg | gaatccaaac | 360 |
| cgtgagcttt | ccgaggattg | cctctacctt | aacgtgtgga | ctccataccc | aaggccaact | 420 |
| tctccaactc | cagttctcgt | ttggatctac | ggtggtggat | tctactccgg | tgcttcttct | 480 |
| ctcgatgtgt | acgatggaag | attcctcgtt | caggctgaga | ggactgtgct | cgtgtctatg | 540 |
| aattacaggg | tgggagcttt | cggattcctt | gctttgccag | gatctagaga | ggctccaggt | 600 |
| aacgttggac | ttcttgatca | aaggcttgct | ctccagtggg | tgcaagagaa | tgttgctgct | 660 |
| tttggaggcg | atccaacttc | cgtgactctt | ttcggagaat | ctgctggtgc | tgcttctgtg | 720 |
| ggaatgcacc | ttttgtctcc | accatctagg | ggacttttcc | acaggctgtc | tcttcaatct | 780 |
| ggtgctccaa | atggaccttg | ggctactgtt | ggaatgggag | aggctagaag | aagggctact | 840 |
| cagcttgctc | atcttgttgg | atgtccacca | ggtggaactg | gtggaaacga | tactgagctt | 900 |
| gttgcttgcc | ttaggactag | gccagctcag | gttttggtta | atcacgagtg | gcacgtgctc | 960 |
| ccacaagagt | ctgttttcag | gttctctttc | gtgcctgtgg | tggatggcga | tttcctctct | 1020 |
| gatactcctg | aagctctcat | caacgctggt | gatttccacg | gacttcaggt | gttggttgga | 1080 |
| gtggttaagg | atgagggctc | ttacttcctt | gtgtacggtg | ctccaggctt | ctccaaggat | 1140 |
| aacgagtctc | tcatttccag | ggctgagttc | cttgctggtg | ttagggttgg | agttccacag | 1200 |
| gtgtcagatc | ttgctgctga | ggctgttgtg | ctccactaca | ctgattggct | tcacccagaa | 1260 |
| gatccagcta | ggcttaggga | agctctttct | gatgttgtgg | gcgatcataa | cgttgtgtgc | 1320 |
| ccagttgctc | aacttgctgg | tagacttgct | gctcagggtg | ctagggttta | cgcttacgtt | 1380 |
| ttcgagcaca | gggcttccac | tttgtcttgg | ccactttgga | tgggtgttcc | acacggatac | 1440 |
| gagatcgagt | tcatcttcgg | aatcccactc | gatccatccc | gtaactacac | tgctgaggaa | 1500 |
| aagatcttcg | ctcagaggct | catgaggtac | tgggctaatt | ttgctaggac | tggcgatcct | 1560 |
| aacgagccaa | gagatccaaa | ggctccacaa | tggccaccat | atacagctgg | tgctcagcag | 1620 |
| tacgtgtccc | ttgatcttag | accacttgag | gtgagaaggg | gacttagggc | tcaagcttgc | 1680 |
| gctttctgga | acagattcct | tccaaagctc | ctcaacgcta | ctgatactct | cgatgaagct | 1740 |
| gagaggcaat | ggaaggctga | gtttaccgt | tggtcctctt | acatggtgca | ctggaagaac | 1800 |
| cagttcgatc | actactccaa | gcaggatagg | tgctctgatt | tgtga | | 1845 |

<210> SEQ ID NO 2
<211> LENGTH: 1845
<212> TYPE: DNA
<213> ORGANISM: Macaca mulatta

<400> SEQUENCE: 2

```
atgaggcctc ctcagtgcct tcttcatact cctagtcttg cttctcctct tctgctgctg    60
cttctttggc ttcttggtgg tggtgttggt gctgaaggta gagaagatgc tgagcttctt   120
gtgactgtta ggggtggtag gcttaggggt atcaggctta agactcctgg tggtcctgtg   180
tctgctttcc ttggtattcc ttttgctgag cctcctaccg gtcctagaag attttgcct   240 cctgaaccta agcagccttg gtctggtgtt gtggatgcta ctactttcca gagcgtgtgc   300
taccagtatg tggataccct ttaccctggt ttcgagggaa ctgagatgtg aaccctaac    360 agagagctgt ctgaggattg cctgtacctt aatgtgtgga cccccttaccc taggcctact   420 tctcctactc ctgttctggt ttggatctac ggtggtggtt tctacagcgg tgcttcttct   480
ctggatgtgt acgatggtag attcctggtt caggctgaga ggactgtgct ggtgtctatg   540
aattacaggg tgggagcttt cggtttcctt gctttgcctg gttctagaga ggctcctggt   600
aacgttggtc ttttggatca gaggcttgct ctgcagtggg tgcaagaaaa tgttgctgct   660
ttcggtggtc atcctacctc tgtgactctt ttcggtgaat ctgctggtgc tgcttcagtg   720
ggtatgcacc ttttgtctcc accttctagg ggacttttcc acagggctgt tcttcaatct   780
ggtgctccta atggtccttg gctactgtt ggtatgggtg aggctagaag aagggctact   840
cagcttgctc atcttgttgg ttgtcctcca ggtggtactg gtggtaatga tactgagctt   900
gtggcttgcc ttaggaccag acctgctcag gttttggtga acaatgagtg gcacgtgctg   960
cctcaagagt ctgtgtttag gttctctttc gtgcctgtgg tggatggtga tttcctgtct  1020
gatactcctg aggctctgat caacgctggt gattttcacg gacttcaggt tctggttggt  1080
gtggtgaagg atgagggatc ttacttcctt gtgtacggtg ctcctggttt cagcaaggat  1140
aacgagtctc tgatcagcag ggctgagttc cttgctggtg ttagagttgg tgttcctcag  1200
gtgtcagatc ttgctgctga ggctgttgtg cttcactaca ctgattggct gcaccctgaa  1260
gatcctgcta gacttaggga agctctgtct gatgtggtgg gtgatcataa tgttgtgtgc  1320
cctgttgctc agttggctgg tagacttgct gctcaaggtg ctagggttta cgcttacgtt  1380
ttcgagcata gggcttctac ccttttcttgg cctctttgga tgggagtgcc tcacggttat  1440
gagatcgagt tcatcttcgg tatccctctt gatccttcta ggaactacac caccgaggaa  1500
aagatcttcg ctcagaggct gatgaggtac tgggctaatt tgctaggac tggtgatcca   1560 aacgagccta gagatcctaa ggctcctcaa tggcctcctt atacagctgg tgctcagcag  1620
tacgtgagcc ttgatcttag acctcttgag gtgagaaggg gtcttagggc tcaagcttgc  1680
gctttctgga acagattcct gcctaagctt ctgagcgcta ccgatactct tgatgaagct  1740
gagagacagt ggaaggcaga gttccatagg tggtcctctt acatggtgca ctggaagaac  1800
cagttcgatc actacagcaa gcaggatagg tgcagcgatc tttag                  1845
```

<210> SEQ ID NO 3
<211> LENGTH: 1809
<212> TYPE: DNA
<213> ORGANISM: Homo sapiens

<400> SEQUENCE: 3

```
atgcatagca aagtcacaat catatgcatc agatttctct tttggtttct tttgctctgc    60
atgcttattg ggaagtcaca tactgaagat gacatcataa ttgcaacaaa gaatggaaaa   120
gtcagaggga tgaacttgac agttttggt ggcacggtaa cagcctttct tggaattccc    180
tatgcacagc cacctcttgg tagacttcga ttcaaaaagc cacagtctct gaccaagtgg   240
```

```
tctgatattt ggaatgccac aaaatatgca aattcttgct gtcagaacat agatcaaagt      300
tttccaggct tccatggatc agagatgtgg aacccaaaca ctgacctcag tgaagactgt      360
ttatatctaa atgtatggat tccagcacct aaaccaaaaa atgccactgt attgatatgg      420
atttatggtg gtggttttca aactggaaca tcatctttac atgtttatga tgcaagtttt      480
ctggctcggg ttgaaagagt tattgtagtg tcaatgaact atagggtggg tgccctagga      540
ttcttagctt tgccaggaaa tcctgaggct ccagggaaca tgggtttatt tgatcaacag      600
ttggctcttc agtgggttca aaaaaatata gcagcctttg gtggaaatcc taaaagtgta      660
actctctttg gagaaagtgc aggagcagct tcagttagcc tgcatttgct ttctcctgga      720
agccattcat tgttcaccag agccattctg caaagtggat cctttaatgc tccttgggcg      780
gtaacatctc tttatgaagc taggaacaga acgttgaact tagctaaatt gactggttgc      840
tctagagaga atgagactga aataatcaag tgtcttagaa ataaagatcc ccaagaaatt      900
cttctgaatg aagcatttgt tgtcccctat gggactcctt tgtcagtaaa ctttggtccg      960
accgtggatg gtgattttct cactgacatg ccagacatat tacttgaact tggacaattt     1020
aaaaaaaccc agattttggt gggtgttaat aaagatgaag ggacagcttt tttagtctat     1080
ggtgctcctg gcttcagcaa agataacaat agtatcataa ctagaaaaga atttcaggaa     1140
ggtttaaaaa tattttttcc aggagtgagt gagtttggaa aggaatccat ccttttttcat     1200 tacacagact gggtagatga tcagagacct gaaaactacc gtgaggcctt gggtgatgtt     1260
gttggggatt ataatttcat atgccctgcc ttggagttca ccaagaagtt ctcagaatgg     1320
ggaaataatg ccttttttcta ctatttttgaa caccgatcct ccaaacttcc gtggccagaa     1380
tggatgggag tgatgcatgg ctatgaaatt gaatttgtct ttggtttacc tctggaaaga     1440
agagataatt acacaaaagc cgaggaaatt ttgagtagat ccatagtgaa acggtgggca     1500
aattttgcaa aatatgggaa tccaaatgag actcagaaca atagcacaag ctggcctgtc     1560
ttcaaaagca ctgaacaaaa atatctaacc ttgaatacag agtcaacaag aataatgacg     1620
aaactacgtg ctcaacaatg tcgattctgg acatcatttt ttccaaaagt cttggaaatg     1680
acaggaaata ttgatgaagc agaatgggag tggaaagcag gattccatcg ctggaacaat     1740
tacatgatgg actggaaaaa tcaatttaac gattacacta gcaagaaaga aagttgtgtg     1800
ggtctctaa                                                             1809

<210> SEQ ID NO 4
<211> LENGTH: 1809
<212> TYPE: DNA
<213> ORGANISM: Macaca fascicularis

<400> SEQUENCE: 4
atggatagca agtcacaat catatgcatc agattactct tttggtttct tttgctctgc       60
atgcttattg gaaagtcaca tactgaagat gacatcgtaa ttgcaacaaa gaatggaaaa      120
gtcagaggga tgaacttaac agttcttggt ggcacggtaa cagcctttct tggaattccc      180
tatgcacagc cacctcttgg tagacttcga ttcaaaaagc cacagtctct gaccaagtgg      240
tctgatattt ggaatgccac aaaatatgca aattcttgct atcagaacat agatcaaagt      300
tttccaggct tccatggatc agagatgtgg aacccaaaca ctgacctcag tgaagactgt      360
ttatatctaa atgtatggat tccggcacct aaaccaaaaa atgctactgt aatgatatgg      420
atttatggtg gtggttttca gactggaaca tcatctttac atgtttatga tgcaagtttt      480
ctggctcgag ttgaaagagt tattgtagtg tcaatgaact ataggtggg tgcccttgga      540
```

```
ttcttagctt tgccaggaaa tcctgaggct ccagggaaca tgggtttatt tgatcaacag    600
ttggctcttc agtgggttca aaaaaatata gcagcctttg gtggaaatcc taaaagtgta    660
actctctttg gagaaagtgc aggagcagct tcagttagcc tgcatttgct ttctcctgga    720
agccattcat tgttcaccag agccattcta caaagtggat cctctaacgc tccttgggca    780
gtaacatctc tttatgaagc taggaacaga acattgacct tggctaaatt gactggttgc    840
tctagagata tgagactga aatagtcaag tgccttagaa ataaagatcc ccacgaaatt    900
cttctgaatg aagcatttgt tgtcccctat gggactctct tgtcagtaaa cttcggtcca    960
accatggatg tgattttct cactgaaatg ccagacatat tcttgaact tggacaattt    1020 aaaaaaaccc agatattggt gggtgttaat aaagatgaag ggacagcttt tttagtctat    1080
ggtgctcctg gcttcagcaa agataacgat agtatcataa ctagaaacga atttcaggaa    1140
ggtttaaaaa tattttttcc aggcgtgagt gagtttggaa aggaatccat cctttttcat    1200
tacacagact gggtagatga tcagagacct gaaaactacc gtgaggcgtt ggatgatgtt    1260
gttggggatt ataatatcat atgccctgcc ttggagttta ccaagaagtt ctcagaatgg    1320
ggaaataatg cctttttcta ctattttgaa caccgatcct ccaaacttcc gtggccagaa    1380
tggatgggag tgatgcatgg ctatgaaatt gaatttgtct ttggtttacc tctggaaaga    1440
agagttaatt acacaaaagc tgaggaaatt ttgagtagat ccatagtgaa acggtgggca    1500
aattttgcaa aatatgggaa tccaaatggg actcataata atagcacaaa atggcctgtc    1560
ttcaaaagca ctgaacaaaa atatctaacc ttgaatacag agtcatcaag aatattgact    1620
aaactacgtg ctcagcaatg ccgattctgg acatcatttt ttccaaaagt cttggaaatg    1680
acaggaaata ttgatgaagc agaatgggag tggaaagcag gattccatcg ctggagcaat    1740
tacatgatgg actggaaaaa tcaatttaac gattacacta gcaagaaaga agttgtgtg    1800 ggtctctaa                                                            1809

<210> SEQ ID NO 5
<211> LENGTH: 231
<212> TYPE: DNA
<213> ORGANISM: Artificial Sequence
<220> FEATURE:
<223> OTHER INFORMATION: Synthetic Construct

<400> SEQUENCE: 5
atggctgtcc tgaatccaat gactttggga atttatctcc aactcttcct ctgctccatc     60
gtgtcgcagc caactttcat caacagtgtc ctcccaatct cagcagccct tcctggcctg    120
gatcagaaga aacgaggcaa ccacaaagca tgctgcctac tgatgccccc gccaccccca    180
ctcttcccac cgccattctt cgactacaag gacgacgatg acaagtgata a              231

<210> SEQ ID NO 6
<211> LENGTH: 519
<212> TYPE: DNA
<213> ORGANISM: Tombusvirus tomato bushy stunt virus

<400> SEQUENCE: 6
atggaacgag ctatacaagg aaacgacgct agggaacaag ctaacagtga acgttgggat     60
ggaggatcag gaggtaccac ttctcccttc aaacttcctg acgaaagtcc gagttggact    120
gagtggcggc tacataacga tgagacgaat tcgaatcaag ataatcccct tggtttcaag    180
gaaagctggg gtttcgggaa agttgtattt aagagatatc tcagatacga caggacggaa    240
```

```
gcttcactgc acagagtcct tggatcttgg acgggagatt cggttaacta tgcagcatct    300
cgatttttcg gtttcgacca gatcggatgt acctatagta ttcggtttcg aggagttagt    360
atcaccgttt ctggagggtc gcgaactctt cagcatctct gtgagatggc aattcggtct    420
aagcaagaac tgctacagct tgccccaatc gaagtggaaa gtaatgtatc aagaggatgc    480
cctgaaggta ctgagacctt cgaaaaagaa agcgagtaa                           519
```

<210> SEQ ID NO 7
<211> LENGTH: 6
<212> TYPE: PRT
<213> ORGANISM: Unknown
<220> FEATURE:
<223> OTHER INFORMATION: C-terminal sequence present in multiple
      organisms

<400> SEQUENCE: 7

Ser Glu Lys Asp Glu Leu
1               5

<210> SEQ ID NO 8
<211> LENGTH: 4
<212> TYPE: PRT
<213> ORGANISM: Unknown
<220> FEATURE:
<223> OTHER INFORMATION: C-terminal sequence present in multiple
      organisms

<400> SEQUENCE: 8

Lys Asp Glu Leu
1